(12) United States Patent
Jain et al.

(10) Patent No.: US 11,123,420 B2
(45) Date of Patent: Sep. 21, 2021

(54) STABLE LIVE ATTENUATED RECOMBINANT DENGUE VACCINE

(71) Applicant: PANACEA BIOTEC LIMITED, New Delhi (IN)

(72) Inventors: Rajesh Jain, New Delhi (IN); Sukhjeet Singh, New Delhi (IN); Lavit Jambu, New Delhi (IN)

(73) Assignee: PANACEA BIOTEC LIMITED, New Delhi (IN)

( * ) Notice: Subject to any disclaimer, the term of this patent is extended or adjusted under 35 U.S.C. 154(b) by 64 days.

(21) Appl. No.: 15/763,764

(22) PCT Filed: Sep. 29, 2016

(86) PCT No.: PCT/IN2016/000233
§ 371 (c)(1),
(2) Date: Mar. 27, 2018

(87) PCT Pub. No.: WO2017/056101
PCT Pub. Date: Apr. 6, 2017

(65) Prior Publication Data
US 2018/0289793 A1 Oct. 11, 2018

(30) Foreign Application Priority Data
Sep. 30, 2015 (IN) .......................... 3122/DEL/2015

(51) Int. Cl.
| | |
|---|---|
| *A61K 39/12* | (2006.01) |
| *C12N 7/00* | (2006.01) |
| *A61K 47/02* | (2006.01) |
| *A61K 47/26* | (2006.01) |
| *A61K 47/42* | (2017.01) |
| *A61K 39/39* | (2006.01) |
| *A61K 9/00* | (2006.01) |
| *A61K 47/18* | (2017.01) |
| *A61K 9/19* | (2006.01) |
| *A61P 31/14* | (2006.01) |
| *A61K 39/00* | (2006.01) |

(52) U.S. Cl.
CPC ............ *A61K 39/12* (2013.01); *A61K 9/0019* (2013.01); *A61K 9/19* (2013.01); *A61K 39/39* (2013.01); *A61K 47/02* (2013.01); *A61K 47/183* (2013.01); *A61K 47/26* (2013.01); *A61K 47/42* (2013.01); *A61P 31/14* (2018.01); *C12N 7/00* (2013.01); *A61K 2039/5254* (2013.01); *A61K 2039/54* (2013.01); *A61K 2039/70* (2013.01); *C12N 2770/24134* (2013.01); *C12N 2770/24151* (2013.01); *C12N 2770/24171* (2013.01); *Y02A 50/30* (2018.01)

(58) Field of Classification Search
None
See application file for complete search history.

(56) References Cited

U.S. PATENT DOCUMENTS

2016/0151477 A1* 6/2016 Bett ...................... A61K 39/12
424/186.1

FOREIGN PATENT DOCUMENTS

| WO | WO/2008/022196 | * | 2/2008 |
|---|---|---|---|
| WO | WO 2014/083194 | | 6/2014 |

OTHER PUBLICATIONS

Durbin, Anna P., et al.: "rDEN4Δ30, a Live Attenuated Dengue Virus Type 4 Vaccine Candidate, is Safe, Immunogenic, and Highly Infectious in Healthy Adult Volunteers," The Journal of Infectious Diseases, 2005, 191 pp. 710-718.
Monath, Thomas P., et al.: "Live Attenuated Chimeric Yellow Fever Dengue Type 2 (ChimeriVax ™-DEN2) Vaccine: Phase 1 Clinical Trial for Safety and Immunogenicity," Human Vaccines 2:2, 60-67, Mar./Apr. 2006, p. 61.
Simasathien, S., et al.: "Dengue Vaccine." Journal-Medical Association of Thailand, Nov. 25, 2005, 88:S363 Abstract.
Whitehead, Steven S., et al.: "Chemical Mutagenesis of Dengue Virus Type 4 Yields Mutant Viruses Which Are Temperature Sensitive in Vero Cells or Human Liver Cells and Attenuated in Mice," Journal of Virology, Oct. 2001, pp. 9731-9740.
International Search Report issued in International patent application No. PCT/IN2016/000233, dated Mar. 1, 2017.

* cited by examiner

*Primary Examiner* — Benjamin P Blumel
(74) *Attorney, Agent, or Firm* — Seyfarth Shaw LLP; Jamaica P. Szeliga

(57) ABSTRACT

The present invention relates to field of live attenuated recombinant tetravalent dengue vaccines and methods of producing stable compositions. Present invention specifically relates to a stable composition and methods of using such a stable composition comprising live attenuated recombinant dengue virus, stabilizer, bulking agent and optionally buffering agents, wherein the live attenuated dengue virus is generated from Δ 30 and or Δ 31 deleted or mutated dengue strains. More specifically, the present invention relates to stabilizers for freeze-dried live attenuated immunogenic and/or vaccine compositions that may comprise, inter alia, dengue virus(es). The invention further relates to stabilized, freeze-dried live attenuated immunogenic and/or vaccine compositions of, dengue virus(es), which may contain these stabilizers. Other aspects of the invention are described in or are evident from the following disclosure, and are within the ambit of the invention.

22 Claims, No Drawings

STABLE LIVE ATTENUATED RECOMBINANT DENGUE VACCINE

FIELD OF INVENTION

The present invention relates to field of live attenuated recombinant tetravalent dengue vaccines and methods of producing stable compositions. Present invention specifically relates to a stable composition and methods of using such a stable composition comprising live attenuated recombinant dengue virus, stabilizer, bulking agent and optionally buffering agents, wherein the live attenuated dengue virus is generated from Δ 30 and or Δ 31 deleted or mutated dengue strains. More specifically, the present invention relates to stabilizers for freeze-dried live attenuated immunogenic and/or vaccine compositions that may comprise, inter alia, dengue virus(es). The invention further relates to stabilized, freeze-dried live attenuated immunogenic and/or vaccine compositions of, dengue virus(es), which may contain these stabilizers. Other aspects of the invention are described in or are evident from the following disclosure, and are within the ambit of the invention.

BACKGROUND OF THE INVENTION

Dengue virus (DENV) is a member of the Flavivirus genus of the Flaviviriade family which also includes yellow fever virus (YFV), West Nile virus (WNV), Japanese encephalitis virus (JEV) and tick-borne encephalitis virus. Flavivirus genome is single-stranded, positive-sense, RNA molecule of 11 kilobases containing single open reading frame. The RNA is translated into a polyprotein that is processed into at least 10 gene products: 3 structural proteins—Nucleocapsid or Core (C), Premembrane (prM), & Envelope (E) & 7 nonstructural (NS) proteins—NS 1, 2A, 2B, 3, 4A, 4B, & 5. There are four antigenically distinct serotypes (DENV1-4) based on neutralization assay. All the serotypes are competent in causing asymptomatic manifestations as well as the more severe and fatal DHF and DSS. DENV is transmitted to humans mainly by *Aedes* mosquitoes (*Aedes aegypti* and *Aedes albopictus*). The prevalence of dengue disease is high especially in the Asia-Pacific region and the Americas. All four DENV serotypes are now circulating in these areas. With increased international travel and climate change, people are at risk of dengue infection beyond the traditional tropical and subtropical areas. Dengue disease is becoming one of the most important emerging vector-borne viral diseases. In the last 20 years dengue has spread rapidly and is endemic in more than 100 countries. An estimated 50 million dengue infection cases occur globally with around 500,000 cases of severe dengue and 20,000 deaths per year. Approximately, two-fifths of the world's population is at risk from dengue infection. Hence, the prevention and treatment of dengue fever is an important issue for the governments of many countries.

Dengue has become a huge burden both in terms of lives lost, particularly, children and also the economic setback to the emerging economies of the world to contain the disease. A primary infection with any of the serotypes would induce lifetime immunity against that particular serotype but a subsequent infection with a different serotype can increase the severity of the disease due to a phenomenon known as antibody dependent enhancement (ADE). Hence development of an effective vaccine candidate catering to all the four serotypes, which would be safe and cost effective, is of great significance particularly for children and young adults who are the most susceptible.

An ideal dengue vaccine should satisfy several factors to be commercially feasible. First, the vaccine must be protective against each of the four DENV serotypes to reduce the risk of ADE. Second, the immunization should be safe and not cause unacceptable side-effects caused by cross-reactive antibodies or cross-reactive T cells. Third, the cost should be affordable to the individuals who most need the vaccines. There are still several obstacles for the development of dengue vaccines. One is that the complicated pathogenesis is not fully understood. Another hindrance is the lack of suitable animal models.

Currently there are no licensed vaccines available for dengue although there are vaccines available for a number of closely related viruses. The World Health Organization has prioritized the development of dengue vaccine and therapeutics for a long time. But so far due to unsuccessful development of any kind of vaccine or treatment for containing dengue, the arrangements so far pursued have been vector control and individual preventive steps which are tough to sustain and also expensive. The vector control programs are not sufficient to control the spread of the Dengue virus. In the absence of realistic alternatives, the development of a dengue vaccine has become a public health imperative. Similar to other viral vaccines, the success or failure of candidate dengue vaccines may well hinge on neutralizing antibody. Infection with a single DENV type results in a life-long antibody response and solid protection to challenge with the same virus type but still susceptible to other dengue serotypes.

Live attenuated vaccine development efforts are considered one of the effective approaches. A wild type dengue virus can be attenuated by serial passages in tissue culture to be used in humans maintaining its ability to generate an immune response. In another embodiment a chimeric vaccine candidate is generated by modification of a licensed yellow fever virus vaccine with dengue proteins. Another important feature of a live attenuated vaccine is its ability to induce sustained immune responses very closely mimicking a response in case of a natural infection. Several live attenuated dengue vaccine candidates have been developed and evaluated in humans or non-human primates. The first live attenuated dengue vaccine candidates were host range mutants developed by serial passage of wild type dengue viruses in the brains of mice and selection of mutants attenuated for humans (Kimura, R. & Hotta, S. 1944 Japanese J Bacteriology 1:96-99; Sabin, A. B. & Schlesinger, R. W. 1945 Science 101:640; Wisseman, C. L. Jr. et al. 1963 A'n J Trop Med 12:620-623). Although these candidate vaccine viruses were immunogenic in humans, their poor growth in cell culture discouraged further development. Additional live attenuated DEN-1, DEN-2, DEN-3, and DEN-4 vaccine candidates have been developed by serial passage in tissue culture (Angsubhakorn, S. et al. 1994 Southeast Asian J Trop Med Public Health 25:554-9; Bancroft, W. H. et al. 1981 Infect Immuno 31:698-703; Bhamarapravati, N. et al. 1987 Bull World Health Organ 65:189-95; Eckels, K. H. et al. 1984 Am J Trop Med Hyg 33:684-9; 15Hoke, C. H. Jr. et al. 1990 Am J Trop Med Hyg 43:219-26; Kanesa-thasan, N. et al. 2001 Vaccine 19:3179-88) or by chemical mutagenesis (McKee, K. T. Jr. et al. 1987 Am J Trop Med Hyg 36:435-42). It has proven very difficult to achieve a satisfactory balance between attenuation and immunogenicity for each of the four serotypes of dengue virus using these approaches and to formulate a tetravalent vaccine that is safe and satisfactorily immunogenic against each of the four dengue viruses (Kanesa-thasan, N. et al.

2001 Vaccine 19:3179-88; Bhamarapravati, N. & Sutee, Y. 2000 Vaccine 18 Suppl 2: 44-7).

The goal of immunization is to protect against dengue virus disease by the induction of a long-lived neutralizing antibody response against each of the four serotypes. Simultaneous protection against all four serotypes is required, since an increase in disease severity can occur in persons with preexisting antibodies to a heterotypic dengue virus. Such immunization can be achieved economically with a live, attenuated virus vaccine. Applicants have successfully developed such a vaccine as reported in WO1993006214, WO2002095075, WO2003092592 and WO2008022196. At the National Institutes of Health (NIH), Atlanta, USA, attenuation to the wild type dengue virus strains was brought about by a novel 30 nucleotide deletion in the untranslated region at the 3' end of the viral genome. This deletion led to safe and complete attenuation of the virus strains with decreased viremia as observed in several studies in monkeys and humans (Phase I studies with monovalent virus strains).

Immunogenic compositions and vaccine compositions comprising biological ingredients, such as viruses, bacteria, parasites, fungi, proteins, polypeptides, glycoproteins, and especially, attenuated live microorganisms, are markedly sensitive to the conditions by which they are prepared, formulated and stored. Such biological ingredients can be modified and degraded by chemical reactions (e.g. hydrolysis, deamination, Maillard's reaction), many of which are mediated by water. Liquid water allows for molecular movements and can result in modification of protein conformations in compositions comprising biological ingredients. By limiting access to water or by removing water, a major factor of modification and degradation is reduced. Prior methods to confer stability to biological ingredients have primarily involved freezing the water or removing water by freeze-drying.

Dengue viruses are basically thermo-labile in nature and lose infectivity upon exposure to higher temperature. In order to maintain the viability of virus, ultra-storage (usually less that $-60°$ C.) is required. Storage at such a low temperature is not a favorable option in field condition due to supply chain related issues and higher cost associated with such storage temperatures. To be successful in field conditions, the vaccine needs to be stable at 2-8° C. In order to impart thermo-stability to virus, optimal quantity of various excipients, selected from the group of stabilizer, bulking agents, vehicle and buffering agents is required.

Pivotal to the successful use and commercialization of vaccines is the manner by which they are processed and formulated, to ensure stability and maintenance of efficacy under conditions in which the vaccines are shipped and stored prior to use. Lyophilization is an approach involved in the processing of some vaccine products, and is essentially a freeze-drying process that, under low pressures, removes water through sublimation, and leaves the product as a dried cake with a small amount of moisture. This process can be advantageous to vaccines, including live attenuated dengue virus vaccines as described above, because such vaccines tend to be more stable in a low moisture environment. A critical factor impacting the efficacy of the Lyophilization process is the formulation of the vaccine. For example, it is desirable that the formulation, upon removal of water, enhances the stability of the product. Typically, a vaccine formulation will contain any or all of the following components: a bulking agent, a stabilizer, and optionally a buffer. The development of effective and efficient processing methods and formulations is therefore of great importance to the development of clinically useful and commercially successful vaccines, including live attenuated dengue vaccines.

Despite advances in the area of vaccine formulations, there remains a distinct need for dengue live attenuated vaccine formulations with improved stability and shelf-life. None of the compositions known in prior art impart, the desired level of stability. The present invention addresses the unmet need for a live attenuated dengue vaccine formulation with increased stability.

SUMMARY OF THE INVENTION

The present invention describes stable dengue vaccine compositions where the strains of dengue are live attenuated and recombinant. More specifically the present invention describes stable lyophilized dengue vaccine compositions where the strains of dengue are live attenuated and recombinant.

The present invention relates to a stable composition comprising live attenuated recombinant dengue virus, stabilizer, bulking agent and optionally buffering agents.

The present invention further relates to a method of preventing or treating a disease or condition in a subject, the method comprising administering to the subject a composition comprising live, attenuated recombinant dengue virus, stabilizer, bulking agent and optionally buffering agents.

The present invention relates to a stable composition comprising live attenuated recombinant dengue virus, stabilizer, bulking agent and optionally buffering agents, wherein the live attenuated dengue virus are selected from Δ 30 deleted dengue strains which are Dengue 1, Dengue 2, Dengue 4 & Dengue 3/4 or chimeric dengue strains which are Dengue 1/4, Dengue 2/4, Dengue 3/4 & Dengue 4.

The present invention further relates to a method of preventing or treating a disease or condition in a subject, the method comprising administering to the subject a composition comprising live, attenuated dengue virus, stabilizer, bulking agent and optionally buffering agents, wherein the live attenuated dengue virus are selected from Δ 30 deleted dengue strains which are Dengue 1, Dengue 2, Dengue 4 & Dengue 3/4 or chimeric dengue strains which are Dengue 1/4, Dengue 2/4, Dengue 3/4 & Dengue 4.

The present invention relates to a stable composition comprising live attenuated dengue virus, stabilizer, bulking agent and optionally buffering agents, wherein the live attenuated dengue virus comprises Δ30 and/or Δ31 mutations.

The present invention further relates to a method of preventing or treating a disease or condition in a subject, the method comprising administering to the subject a composition comprising live, attenuated dengue virus, stabilizer, bulking agent and optionally buffering agents, wherein the live attenuated dengue virus comprises Δ30 and/or Δ31 mutations.

The present invention relates to a stable composition comprising live attenuated recombinant dengue virus, stabilizer, bulking agent and optionally buffering agents, wherein the live attenuated dengue virus are selected from one or more of Dengue virus serotype 1 (rDEN-1Δ30), Dengue virus serotype 2 (rDEN-2/4Δ30), Dengue virus serotype 3 (rDEN-3Δ30/31), Dengue virus serotype 4 (rDEN-4Δ30).

The present invention further relates to a method of preventing or treating a disease or condition in a subject, the method comprising administering to the subject a composition comprising live, attenuated recombinant dengue virus, stabilizer, bulking agent and optionally buffering agents, wherein the live attenuated dengue virus are selected from one or more of Dengue virus serotype 1 (rDEN-1 Δ30), Dengue virus serotype 2 (rDEN-2/4Δ30), Dengue virus serotype 3 (rDEN-3Δ30/31), Dengue virus serotype 4 (rDEN-4Δ30).

DESCRIPTION OF THE INVENTION

The present invention will be described with reference to certain embodiments but the present invention is not limited thereto but only by the claims.

The term "live" is used in its conventional meaning, a live virus is a virus which has not been inactivated, i.e. a virus capable of replicating on permissive cells. A live attenuated dengue virus is a dengue virus which does not induce the disease caused by the corresponding wild-type virus in animals or humans and which is capable of inducing a specific immune response.

The term Δ30 mutation relates to strains created in dengue virus by the removal of 30 nucleotides from the 3'-UTR. The term Δ31 mutation relates to strains created in dengue virus by the removal of 31 nucleotides from the 3'-UTR. Δ30/31 mutation includes the original Δ30 mutation and a non-contiguous 31 nt deletion. The Δ31 mutation can also be generated alone to discern the contribution of either Δ30 or Δ31 in the combined Δ30/31 deletion mutation. Contents of WO2008022196 are incorporated herein in entirety As used herein, the terms "virus chimera," "chimeric virus," "dengue chimera" and "chimeric dengue virus" means an infectious construct of the invention comprising nucleotide sequences encoding the immunogenicity of a dengue virus of one serotype and further nucleotide sequences derived from the backbone of a dengue virus of a different serotype.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments As used herein, the terms "immunogenic composition" and "immunological composition" and "immunogenic or immunological composition" cover any composition that elicits an immune response against the antigen or immunogen of interest expressed from vectors; for instance, after administration into a subject, elicits an immune response against the targeted immunogen or antigen of interest. The terms "vaccinal composition" and "vaccine" and "vaccine composition" covers any composition that induces a protective immune response against the antigen of interest, or which efficaciously protects against the antigen; for instance, after administration or injection into the subject, elicits a protective immune response against the targeted antigen or immunogen or provides efficacious protection against the antigen or immunogen expressed from vectors.

As used herein "Freeze-drying" involves Lyophilization and refers to the process by which a suspension is frozen, after which the water is removed by sublimation at low pressure. As used herein, the term "sublimation" refers to a change in the physical properties of a composition, wherein the composition changes directly from a solid state to a gaseous state without becoming a liquid.

"Human serum albumin" or "HSA" refers to a non-glycosylated monomeric protein consisting of 585 amino acid residues, with a molecular weight of 66 kD. Its globular structure is maintained by 17 disulphide bridges, which create a sequential series of 9 double loops. HSA may also be called human plasma albumin. All variants of human serum albumin are within the scope of the present invention.

The term "collagen" as used herein refers to all forms of collagen from any source including, but not limited to, collagen extracted from tissue or produced recombinantly, collagen analogues, collagen derivatives, modified collagens, and denatured collagens such as gelatin. For example, collagen may be extracted and purified from animal tissue including human or other mammalian sources, such as bovine or porcine corium and human placenta, or may be recombinantly or otherwise produced. The preparation of purified, substantially non-antigenic collagen in solution from animal sources such as bovine and porcine sources is within the purview of those skilled in the art. For example, collagen, including Type I collagen, may be extracted from pig dermis via an acid pH solubilization or via a pepsin digestion and purified with saline precipitations, utilizing processes within the purview of those skilled in the art. Collagen of any type, including, but not limited to, types I, II, III, IV, or any combination thereof, may be used in the formulations of the present disclosure.

As used herein, "hydrolyzed collagen" is defined as a collagen hydrolysate polypeptide having a molecular weight lower than native collagen, i.e., in the 100 to 300,000 Daltons range, and is derived by hydrolysis. Hydrolyzed collagen is commercially available in powdered form or an aqueous solution. Commercial preparation is typically accomplished by one of four methods: (1) alkaline hydrolysis; (2) enzymatic hydrolysis; (3) acid hydrolysis; and (4) synthetically by fermentation. Any of these methods can be used to derive the hydrolyzed collagen from either a bovine (bone and skin preferred), porcine, fish, avian or a synthetic source.

"Gelatin" as used herein is a derivative of collagen, a principal structural and connective protein in animals. Gelatin is derived from denaturation of collagen and contains polypeptide sequences having Gly-X-Y repeats, where X and Y are most often proline and hydroxyproline residues. These sequences contribute to triple helical structure and affect the gelling ability of gelatin polypeptides. Currently available gelatin is extracted through processing of animal hides and bones, typically from bovine and porcine sources. The term hydrolyzed gelatin, as used herein, denotes a gelatin in which some of the peptide bonds have been broken by acids or enzymes. Both natural and recombinant versions of gelain and hydrolyzed gelatin are within the scope of the present invention.

Also with the scope are collagens or gelatin like peptide components.

Live-attenuated vaccines are replication-competent viruses, which can induce an immune response and an immune memory that are comparable to those induced by the wild-type virus. Live-attenuated viruses do not cause disease because of the low level of replication and hence low levels of inflammation. Prominent examples of successful live-attenuated vaccines providing long-term immunity are those against vaccinia virus, poliovirus (Sabin), and two members of the Flaviviridae family, yellow fever virus (YF-17D) and Japanese encephalitis virus (JEV SA14-14-2). Live-attenuated dengue vaccines have been shown to induce protective neutralizing antibody titers in mice, monkeys, and humans. In addition, evidence that a balanced T cell response contributes to protection is accumulating, emphasizing the importance of T cell epitopes in a vaccine.

A live attenuated vaccine or immunogenic composition has the following advantages: it can be administered in low doses, particularly if it is self-replicating; it closely mimics the natural/wild-type infection in a subject, and it provides to the subject all possible immunologically important antigens at the same time, i.e., in a single administration. It is generally agreed that immunogenic compositions or vaccine compositions based on live attenuated microorganisms have the ability to induce a highly effective type of immune response. Such immunogenic compositions or vaccine compositions have the advantage that, once the animal host has been immunized, entry of the pathogen into the host induces an accelerated recall of earlier, cell-mediated or humoral immunity, which is able to control the further growth of the organism before the infection can assume clinically significant proportions. Immunogenic compositions or vaccine compositions based on a killed pathogen (killed vaccine) are generally conceded in the art to be unable or less likely to achieve this type of response. However, immunogenic compositions or vaccine compositions that contain a live pathogen, depending on the level of attenuation, present the danger that the immunized host, upon immunization, can contract the disease against the protection is being sought. Therefore, immunogenic compositions or vaccine compositions that possess the immunizing attributes of a live pathogen, but that is incapable of causing undesirable side effects upon administration to a subject would be highly desirable.

The vaccines according to the present invention are characterized by being tetravalent and containing a common nucleotide deletion in the 3' untranslated region of dengue types 1, 2, 3, and comprising a nucleic acid comprising a first nucleotide sequence encoding at least one structural protein from a first dengue virus and a second nucleotide sequence encoding nonstructural proteins from a second dengue virus, wherein the second dengue virus is attenuated by a deletion of about 30 nucleotides from the 3' untranslated region of the dengue genome corresponding to the TL2 stem-loop structure. The vaccines according to the present invention are prepared by using dengue virus or chimeric dengue virus comprising a mutation in the 3"untranslated region (3-UTR) selected from the group consisting of: (a) a Δ30 mutation that removes the TL-2 homologous structure in each of the dengue virus serotypes 1, 2, 3, and 4, and nucleotides additional to the Δ30 mutation deleted from the 3'-UTR that removes sequence in the 5' direction as far as the 5' boundary of the TL-3 homologous structure in each of the dengue virus serotypes 1, 2, 3, and 4; and (b) a replacement of the 3'-UTR of a dengue virus of a first serotype with the 3'-UTR of a dengue virus of a second serotype, optionally containing the Δ30 mutation and nucleotides additional to the Δ30 mutation deleted from the 3-UTR.

The strains that are preferred for the formulations according to the instant invention are flavivirus having a phenotype in which the viral genome is modified by the introduction of a mutation, singly or in combination, taken from the group consisting of the mutations of any of Table 1-37 of WO02095075A1. More specifically temperature-sensitive, host-range restricted mutant flavivirus, designated mutant 200, 201, wherein said virus comprises charge-cluster-to-alanine mutations at amino acids 2687 and 2688 of the NS5 gene, where amino acid position is given for the polyprotein of dengue virus type 4, optionally further comprising the Δ30 mutation. The strains according to the current invention may be attenuated dengue virus comprising a mutation at nucleotide position 4995 of the NS3 gene; wherein said numbering is based upon a prototypical DEN4 isolate strain 814669 (Dominica 1981); wherein said mutation results in a nucleotide substitution from T to C; and wherein said attenuated dengue virus is attenuated as compared to a wildtype dengue virus, further optionally comprising a Δ30 mutation or attenuated dengue virus comprising a mutation wherein the mutation results in the expression of an NS3 protein having an amino acid substitution from serine or asparagine to proline at amino acid position 1632; wherein said numbering is based upon a viral polypeptide encoded by a prototypical DEN4 isolate strain 814669 (Dominica 1981); wherein said attenuated dengue virus is attenuated as compared to a wildtype dengue virus.

More specifically the instant invention relates to a immunogenic composition being tetravalent and containing a common nucleotide deletion in the 3' untranslated region of dengue types 1, 2, 3, and comprising a nucleic acid comprising a first nucleotide sequence encoding at least one structural protein from a first dengue virus and a second nucleotide sequence encoding nonstructural proteins from a second dengue virus, wherein the second dengue virus is attenuated by a deletion of about 30 nucleotides from the 3' untranslated region of the dengue genome corresponding to the TL2 stem-loop structure, optionally comprising a mutation selected from the group consisting of temperature sensitivity in Hero cells or the human liver cell line HuH-7, host cell restriction in mosquito cells or the human liver cell line HuH-7, host-cell adaptation for 25 improved replication in Nero cells, or attenuation in mice or monkeys, the composition comprising a member selected from the group consisting of: (1) rDEN130' rDEN230, rDEN3630, rDEN430, (2) rDEN1630, rDEN2630, rDEN3630, rDEN4/1Λ30, (3) rDEN130, rDEN230, rDEN3630, rDEN4/2630, 30 (4) rDEN1630, rDEN230, rDEN3630, rDEN4/3630, (5) rDEN1630, rDEN2630, rDEN3/1630, rDEN430, (6) rDEN1630, rDEN2630, rDEN3/130, rDEN4/1630,-118 (7) rDEN130, rDEN230, rDEN3/130, rDEN4/2630, (8) rDEN1630, rDEN230, rDEN3/1630, rDEN4/3630, (9) rDEN130, rDEN2630, rDEN3/2630, rDEN4630, (10) rDEN1630, rDEN2630, rDEN3/230, rDEN4/1630, 5 (11) rDEN1630, rDEN2630, rDEN3/2630, rDEN4/2630, (12) rDEN1630, rDEN2630, rDEN3/2630, rDEN4/3630, (13) rDEN130, rDEN2630, rDEN3/4630, rDEN430, (14) rDEN130, rDEN2630, rDEN3/4630, rDEN4/1630, (15) rDEN130, rDEN230, rDEN3/4630, rDEN4/2630, (16) rDEN1630, rDEN230, rDEN3/430, rDEN4/3630, (17) rDEN1630, rDEN2/130, rDEN3630, rDEN4630, (18) rDEN1Λ30, rDEN2/130, rDEN3630, rDEN4/130, (19) rDEN130, rDEN2/130, rDEN3630, rDEN4/2630, (20) rDEN1630, rDEN2/130, rDEN3630, rDEN4/3630, (21) rDEN1630, rDEN2/1630, rDEN3/1630, rDEN430, (22) rDEN1630, rDEN2/130, rDEN3/1630, rDEN4/1630, (23) rDEN130, rDEN2/130, rDEN3/1630, rDEN4/2630, (24) rDEN1630, rDEN2/130, rDEN3/1630, rDEN4/3630, (25) rDEN130, rDEN2/1630, rDEN3/2630, rDEN4630, 20 (26) rDEN1630, rDEN2/130, rDEN3/2630, rDEN4/1630, (27) rDEN130, rDEN2/130, rDEN3/2630, rDEN4/2630, (28) rDEN1630, rDEN2/130, rDEN3/2630, rDEN4/3630, (29) rDEN1630, rDEN2/1630, rDEN3/4630, rDEN430, (30) rDEN1630, rDEN2/1630, rDEN3/4630, rDEN4/130, (31) rDEN1630, rDEN2/130, rDEN3/4630, rDEN4/2630, (32) rDEN130, rDEN2/1Λ30, rDEN3/4630, rDEN4/3630, (33) rDEN1630, rDEN2/330, rDEN330, rDEN430, (34) rDEN130, rDEN2/330, rDEN330, rDEN4/1630, (35) rDEN130, rDEN2/330, rDEN3630, rDEN4/2630, 30 (36) rDEN1630, rDEN2/330, rDEN3630, rDEN4/330, (37) rDEN1630, rDEN2/3630, rDEN3/1630, rDEN4630, (38)

rDEN1630, rDEN2/330, rDEN3/1630, rDEN4/1630,-119 (39) rDEN130, rDEN2/330, rDEN3/130, rDEN4/230, (40) rDEN1630, rDEN2/3630, rDEN3/130, rDEN4/3630, (41) rDEN130, rDEN2/3630, rDEN3/2630, rDEN430, (42) rDEN1630, rDEN2/3630, rDEN3/2630, rDEN4/1630, 5 (43) rDEN1/\30, rDEN2/330, rDEN3/2630, rDEN4/23O, (44) rDEN1630, rDEN2/330, rDEN3/230, rDEN4/3630, (45) rDEN163O, rDEN2/33O, rDEN3/43O, rDEN463O, (46) rDEN13O, rDEN2/363O, rDEN3/463O, rDEN4/13O, (47) rDEN163O, rDEN2/33O, rDEN3/463O, rDEN4/23O, 10 (48) rDEN13O, rDEN2/363O, rDEN3/463O, rDEN4/363O, (49) rDEN13O, rDEN2/430, rDEN33O, rDEN4630, (50) rDEN1630, rDEN2/430, rDEN3630, rDEN4/163O, (51) rDEN163O, rDEN2/463O, rDEN363O, rDEN4/23O, (52) rDEN13O, rDEN2/43O, rDEN33O, rDEN4/363O, 15 (53) rDEN13O, rDEN2/463O, rDEN3/163O, rDEN43O, (54) rDEN163O, rDEN2/43O, rDEN3/13O, rDEN4/163O, (55) rDEN163O, rDEN2/43O, rDEN3/163O, rDEN4/263O, (56) rDEN163O, rDEN2/463O, rDEN3/163O, rDEN4/363O, (57) rDEN163O, rDEN2/43O, rDEN3/263O, rDEN43O, 20 (58) rDEN13O, rDEN2/463O, rDEN3/263O, rDEN4/13O, (59) rDEN163O, rDEN2/463O, rDEN3/263O, rDEN4/263O, (60) rDEN13O, rDEN163O, rDEN2/43O, rDEN3/263O, rDEN4/363O, (61) rDEN163O, rDEN2/43O, rDEN3/463O, rDEN463O, (62) rDEN163O, rDEN2/463O, rDEN3/43O, rDEN4/163O, 25 (63) rDEN163O, rDEN2/463O, rDEN3/463O, rDEN4/263O, (64) rDEN13O, rDEN2/4/\3O, rDEN3/43O, rDEN4/33O, (65) rDEN1/263O, rDEN263O, rDEN363O, rDEN43O, (66) rDEN1/23O, rDEN2/\3O, rDEN363O, rDEN4/163O, (67) rDEN1/263O, rDEN23O, rDEN33O, rDEN4/23O, (68) rDEN1/263O, rDEN23O, rDEN33O, rDEN4/363O, (69) rDEN1/23O, rDEN23O, rDEN3/163O, rDEN463O, (70) rDEN1/23O, rDEN263O, rDEN3/163O, rDEN4/163O,-120 (71) rDEN1/230, rDEN230, rDEN3/1630, rDEN4/2630, (72) rDEN1/230, rDEN2630, rDEN3/130, rDEN4/3630, (73) rDEN1/2630, rDEN2630, rDEN3/230, rDEN430, (74) rDEN1/2/30, rDEN2630, rDEN3/230, rDEN4/1630, 5 (75) rDEN1/230, rDEN2630, rDEN3/2630, rDEN4/2630, (76) rDEN1/2630, rDEN2630, rDEN3/230, rDEN4/3630, (77) rDEN1/2\30, rDEN2630, rDEN3/430, rDEN4630, (78) rDEN1/230, rDEN2630, rDEN3/430, rDEN4/1630, (79) rDEN1/230, rDEN2630, rDEN3/430, rDEN4/2630, 10 (80) rDEN1/2/\30, rDEN2630, rDEN3/430, rDEN4/3630, (81) rDEN1/230, rDEN2/130, rDEN3630, rDEN4630, (82) rDEN1/230, rDEN2/1630, rDEN3630, rDEN4/1630, (83) rDEN1/2630, rDEN2/130, rDEN330, rDEN4/2630, (84) rDEN1/230, rDEN2/1630, rDEN3630, rDEN4/363O, 15 (85) rDEN1/230, rDEN2/1/\30, rDEN3/1630, rDEN4630, (86) rDEN1/230, rDEN2/1630, rDEN3/1630, rDEN4/1630, (87) rDEN1/230, rDEN2/130, rDEN3/1630, rDEN4/2630, (88) rDEN1/230, rDEN2/130, rDEN3/1630, rDEN4/330, (89) rDEN1/2/\30, rDEN2/1630, rDEN3/2630, rDEN4630, 20 (90) rDEN1/230, rDEN2/130, rDEN3/230, rDEN4/130, (91) rDEN1/2630, rDEN2/1630, rDEN3/2630, rDEN4/230, (92) rDEN1/230, rDEN2/1630, rDEN3/2630, rDEN4/3630, (93) rDEN1/2630, rDEN2/1630, rDEN3/430, rDEN4630, (94) rDEN1/2\30, rDEN2/1630, rDEN3/430, rDEN4/1630, 25 (95) rDEN1/230, rDEN2/1630, rDEN3/4630, rDEN4/23O, (96) rDEN1/230, rDEN2/1630, rDEN3/430, rDEN4/3630, (97) rDEN1/230, rDEN2/330, rDEN3630, rDEN4630, (98) rDEN1/230, rDEN2/330, rDEN3\30, rDEN4/1630, (99) rDEN1/230, rDEN2/330, rDEN330, rDEN4/2630, 30 (100) rDEN1/230, rDEN2/2630, rDEN3630, rDEN4/3630, (101) rDEN1/230, rDEN2/3630, rDEN3/1630, rDEN4630, (102) rDEN1/230, rDEN2/3630, rDEN3/1630, rDEN4/130,-121 (103) rDEN1/2630, rDEN2/3630, rDEN3/1630, rDEN4/2630, (104) rDEN1/2630, rDEN2/3630, rDEN3/1630, rDEN4/3630, (105) rDEN1/230, rDEN2/330, rDEN3/2630, rDEN430, (106) rDEN1/230, rDEN2/330, rDEN3/2630, rDEN4/130, 5 (107) rDEN1/2630, rDEN2/3630, rDEN3/2630, rDEN4/2630, (108) rDEN1/2630, rDEN2/3630, rDEN3/2630, rDEN4/330, (109) rDEN1/2630, rDEN2/3630, rDEN3/4630, rDEN4630, (110) rDEN1/2630, rDEN2/3630, rDEN3/430, rDEN4/1630, (111) rDEN1/230, rDEN2/330, rDEN3/430, rDEN4/2630, 10 (112) rDEN1/230, rDEN2/330, rDEN3/430, rDEN4/330, (113) rDEN1/2630, rDEN2/4630, rDEN3630, rDEN4630, (114) rDEN1/2630, rDEN2/4630, rDEN3630, rDEN4/1630, (115) rDEN1/230, rDEN2/4630, rDEN3630, rDEN4/230, (116) rDEN1/2630, rDEN2/4630, rDEN3630, rDEN4/3630, 15 (117) rDEN1/230, rDEN2/430, rDEN3/130, rDEN4630, (118) rDEN1/2630, rDEN2/4630, rDEN3/1630, rDEN4/130, (119) rDEN1/230, rDEN2/4630, rDEN3/1630, rDEN4/2630, (120) rDEN1/2630, rDEN2/4630, rDEN3/130, rDEN4/330, (121) rDEN1/2630, rDEN2/4630, rDEN3/230, rDEN4630, (122) rDEN1/2630, rDEN2/430, rDEN3/2630, rDEN4/1630, (123) rDEN1/230, rDEN2/430, rDEN4/230, (124) rDEN1/2630, rDEN2/4630, rDEN3/230, rDEN4/330, (125) rDEN1/2630, rDEN2/4630, rDEN3/4630, rDEN430, (126) rDEN1/230, rDEN2/4630, 430, rDEN4/1630, 25 (127) rDEN1/230, rDEN2/4630, rDEN3/4630, rDEN4/2630, (128) rDEN1/230, rDEN2/4630, rDEN3/4630, rDEN4/3630, (129) rDEN1/3630, rDEN2630, rDEN3630, rDEN4630, (130) rDEN1/330, rDEN2630, rDEN330, rDEN4/1630, (131) rDEN1/3630, rDEN230, rDEN3630, rDEN4/2630, 30 (132) rDEN1/3630, rDEN2630, rDEN3630, rDEN4/3630, (133) rDEN1/3630, rDEN2630, rDEN3/1630, rDEN4630, (134) rDEN1/3630, rDEN230, rDEN3/1630, rDEN4/130,-122 (135) rDEN1/3630, rDEN2630, rDEN3/130, rDEN4/230, (136) rDEN1/330, rDEN2630, rDEN3/1630, rDEN4/3630, (137) rDEN1/3630, rDEN230, rDEN3/2630, rDEN4630, (138) rDEN1/3630, rDEN2630, rDEN3/2630, rDEN4/1630, 5 (139) rDEN1/3630, rDEN2630, rDEN3/2630, rDEN4/230, (140) rDEN1/3630, rDEN230, rDEN3/230, rDEN4/3630, (141) rDEN1/3630, rDEN2630, rDEN3/430, rDEN4630, (142) rDEN1/3630, rDEN230, rDEN3/430, rDEN4/1630, (143) rDEN1/330, rDEN2630, rDEN3/4630, rDEN4/230, 10 (144) rDEN1/3630, rDEN2630, rDEN3/430, rDEN4/3630, (145) rDEN1/330, rDEN2/1630, rDEN3630, rDEN4630, (146) rDEN1/330, rDEN2/1630, rDEN3630, rDEN4/1630, (147) rDEN1/3630, rDEN2/1630, rDEN330, rDEN4/2630, (148) rDEN1/330, rDEN2/1630, rDEN3630, rDEN4/330, 15 (149) rDEN1/330, rDEN2/130, rDEN3/1630, rDEN4630, (150) rDEN1/330, rDEN2/1630, rDEN3/130, rDEN4/1630, (151) rDEN1/3630, rDEN2/1630, rDEN3/130, rDEN4/2630, (152) rDEN1/3630, rDEN2/1630, rDEN3/130, rDEN4/330, (153) rDEN1/330, rDEN2/1630, rDEN3/2630, rDEN4630, 20 (154) rDEN1/330, rDEN2/1630, rDEN3/230, rDEN4/130, (155) rDEN1/3630, rDEN2/130, rDEN3/2630, rDEN4/2630, (156) rDEN1/3630, rDEN2/130, rDEN3/230, rDEN4/3630, (157) rDEN1/330, rDEN2/130, rDEN3/4630, rDEN430, (158) rDEN1/3630, rDEN2/1630, rDEN3/430, rDEN4/1630, 25 (159) rDEN1/330, rDEN2/1630, rDEN3/4630, rDEN4/230, (160) rDEN1/330, rDEN2/1630, rDEN3/4630, rDEN4/330, (161) rDEN1/330, rDEN2/3630, rDEN3630, rDEN4630, (162) rDEN1/330, rDEN2/3630, rDEN330, rDEN4/130, (163) rDEN1/3630, rDEN2/3630, rDEN3630, rDEN4/2630, 30 (164) rDEN1/3630, rDEN2/3630, rDEN330, rDEN4/330, (165) rDEN1/3630, rDEN2/3630, rDEN3/1630, rDEN4630, (166) rDEN1/330, rDEN2/330, rDEN3/130, rDEN4/1630,-123 (167) rDEN1/3630, rDEN2/3630, rDEN3/1630, rDEN4/

2630, (168) rDEN1/330, rDEN2/330, rDEN3/1630, rDEN4/330, (169) rDEN1/330, rDEN2/330, rDEN3/230, rDEN430, (170) rDEN1/330, rDEN2/330, rDEN3/230, rDEN4/130, 5 (171) rDEN1/330, rDEN2/3630, rDEN3/2630, rDEN4/2630, (172) rDEN1/3630, rDEN2/330, rDEN3/2630, rDEN4/330, (173) rDEN1/3630, rDEN2/3630, rDEN3/4630, rDEN430, (174) rDEN1/330, rDEN2/3630, rDEN3/4630, rDEN4/130, (175) rDEN1/3,\30, rDEN2/3630, rDEN3/4630, rDEN4/2630, 10 (176) rDEN1/330, rDEN2/3630, rDEN3/4630, rDEN4/3630, (177) rDEN1/3630, rDEN2/4630, rDEN3630, rDEN4630, (178) rDEN1/3630, rDEN2/4630, rDEN3630, rDEN4/1630, (179) rDEN1/3630, rDEN2/4630, rDEN3630, rDEN4/2630, (180) rDEN1/3630, rDEN2/4630, rDEN3630, rDEN4/330, 15 (181) rDEN1/3630, rDEN2/4630, rDEN3/1630, rDEN430, (182) rDEN1/330, rDEN2/430, rDEN3/130, rDEN4/1630, (183) rDEN1/3630, rDEN2/4630, rDEN3/1630, rDEN4/2630, (184) rDEN1/3630, rDEN2/4630, rDEN3/1630, rDEN4/330, (185) rDEN1/3630, rDEN2/4630, rDEN3/230, rDEN430, (186) rDEN1/330, rDEN2/4630, rDEN3/230, rDEN4/1630, 20 (187) rDEN1/330, rDEN2/430, rDEN3/2630, rDEN4/230, (188) rDEN1/3630, rDEN2/430, rDEN3/230, rDEN4/330, (189) rDEN1/3630, rDEN2/4630, rDEN3/4630, rDEN4630, (190) rDEN1/3630, rDEN2/430, rDEN3/4630, rDEN4/1630, (191) rDEN1/330, rDEN2/430, rDEN3/430, rDEN4/230, (192) rDEN1/3630, rDEN2/4630, rDEN3/430, rDEN4/330, (193) rDEN1/4630, rDEN2630, rDEN3630, rDEN430, (194) rDEN1/4630, rDEN2630, rDEN330, rDEN4/1630, (195) rDEN1/4630, rDEN230, rDEN3630, rDEN4/2630, (196) rDEN1/4630, rDEN230, rDEN330, rDEN4/3630, (197) rDEN1/430, rDEN230, rDEN3/130, rDEN4630, (198) rDEN1/430, rDEN230, rDEN3/1630, rDEN4/1630, (199) rDEN1/4630, rDEN2630, rDEN3/130, rDEN4/230, (200) rDEN1/4\30, rDEN2630, rDEN3/130, rDEN4/3630, (201) rDEN1/430, rDEN2630, rDEN3/2630, rDEN430, (202) rDEN1/430, rDEN230, rDEN3/230, rDEN4/130, 5 (203) rDEN1/430, rDEN2630, rDEN3/2630, rDEN4/2630, (204) rDEN1/4/30, rDEN230, rDEN3/2630, rDEN4/330, (205) rDEN1/4630, rDEN230, rDEN3/4630, rDEN4630, (206) rDEN1/4630, rDEN2630, rDEN3/4630, rDEN4/130, (207) rDEN1/4630, rDEN2630, rDEN3/4630, rDEN4/2630, 10 (208) rDEN1/4630, rDEN230, rDEN3/4630, rDEN4/3630, (209) rDEN1/430, rDEN2/1630, rDEN3630, rDEN4630, (210) rDEN1/4630, rDEN2/1630, rDEN3630, rDEN4/130, (211) rDEN1/430, rDEN2/1630, rDEN330, rDEN4/2630, (212) rDEN1/430, rDEN2/1630, rDEN3630, rDEN4/3630, 15 (213) rDEN1/4630, rDEN2/1630, rDEN3/1630, rDEN4630, (214) rDEN1/430, rDEN2/1630, rDEN3/130, rDEN4/1630, (215) rDEN1/4630, rDEN2/1630, rDEN3/130, rDEN4/230, (216) rDEN1/4A30, rDEN2/1630, rDEN3/130, rDEN4/330, (217) rDEN1/430, rDEN2/1630, rDEN3/230, rDEN4430, 20 (218) rDEN1/4630, rDEN2/1630, rDEN3/230, rDEN4/1630, (219) rDEN1/4630, rDEN2/1630, rDEN3/230, rDEN4/2630, (220) rDEN1/430, rDEN2/1630, rDEN3/230, rDEN4/3630, (221) rDEN1/4630, rDEN2/1630, rDEN3/430, rDEN4630, (222) rDEN1/4630, rDEN2/1630, rDEN3/4630, rDEN4/130, (223) rDEN1/430, rDEN2/1630, rDEN3/430, rDEN4/2630, (224) rDEN1/430, rDEN2/1630, rDEN3/4630, rDEN4/3/\30, (225) rDEN1/430, rDEN2/3630, rDEN330, rDEN4630, (226) rDEN1/430, rDEN2/3630, rDEN330, rDEN4/130, (227) rDEN1/430, rDEN2/3630, rDEN3630, rDEN4/2630, 30 (228) rDEN1/430, rDEN2/3630, rDEN3630, rDEN4/3630, (229) rDEN1/430, rDEN2/3630, rDEN3/1630, rDEN430, (230) rDEN1/4630, rDEN2/330, rDEN3/130, rDEN4/1630,-125 (231) rDEN1/4630, rDEN2/3630, rDEN3/1630, rDEN4/2630, (232) rDEN1/4630, rDEN2/330, rDEN3/1630, rDEN4/330, (233) rDEN1/4630, rDEN2/330, rDEN3/2630, rDEN4630, (234) rDEN1/4630, rDEN2/330, rDEN3/2630, rDEN4/130, 5 (235) rDEN1/4630, rDEN2/3630, rDEN3/230, rDEN4/230, (236) rDEN1/4630, rDEN2/3630, rDEN3/230, rDEN4/330, (237) rDEN1/4630, rDEN2/3630, rDEN3/430, rDEN4630, (238) rDEN1/4ΔA30, rDEN2/3630, rDEN3/430, rDEN4/130, (239) rDEN1/430, rDEN2/330, rDEN3/430, rDEN4/230, 10 (240) rDEN1/4630, rDEN2/3630, rDEN3/430, rDEN4/330, (241) rDEN1/4630, rDEN2/430, rDEN3630, rDEN4630, (242) rDEN1/4630, rDEN2/4630, rDEN3630, rDEN4/1630, (243) rDEN1/4630, rDEN2/4630, rDEN3630, rDEN4/230, (244) rDEN1/430, rDEN2/4630, rDEN3630, rDEN4/3630, (245) rDEN1/4630, rDEN2/4630, rDEN3/1630, rDEN430, (246) rDEN1/42\30, rDEN2/4630, rDEN3/1630, rDEN4/130, (247) rDEN1/4630, rDEN2/430, rDEN3/130, rDEN4/230, (248) rDEN1/4630, rDEN2/4630, rDEN3/130, rDEN4/330, (249) rDEN1/430, rDEN2/4630, rDEN3/2630, rDEN4630, (250) rDEN1/430, rDEN2/4630, rDEN3/2630, rDEN4/1630, (251) rDEN1/430, rDEN2/4630, rDEN3/2630, rDEN4/230, (252) rDEN1/430, rDEN2/4630, rDEN3/230, rDEN4/330, (253) rDEN1/4630, rDEN2/4630, rDEN3/430, rDEN4630, (254) rDEN1/4/\30, rDEN2/430, rDEN3/4630, rDEN4/130, (255) rDEN1/4630, rDEN2/4630, rDEN3/430, rDEN4/2630, and (256) rDEN1/4630, rDEN2/4630, rDEN3/4630, rDEN4/330.

Lyophilization, or the process of freeze-drying, is a commonly used technique to remove water in the preparation of dehydrated products. Generally, "freeze-drying" an aqueous composition involves three steps. First, the aqueous composition is frozen under conditions of low temperature. Secondly, the frozen water is removed by sublimation under conditions of reduced pressure and low temperature. At this stage, the composition usually contains about 15% water. Third, the residual water is further removed by desorption under conditions of reduced pressure and higher temperatures. At the end of the Lyophilization process, a freeze-dried product, also called a "pastille" or "cake" is produced. The freeze-dried product contains very low residual water (from about 0.2% to about 5% weight/weight) and dry material in a predominantly amorphous form.

However, substantial loss of immunogenic activity of biological ingredients are observed during the preparation stages, such as before and during Lyophilization, and also during storage of immunogenic compositions and vaccine compositions. The integrity of biological ingredients must be safeguarded to ensure that the immunization efficiency of immunogenic compositions and vaccine compositions is retained. The immunogenic activity of biological ingredients is measured by the ability to induce and stimulate an immunologic response when administered to a host or subject.

To limit the manipulation of subjects and the number of administrations, there is a strong need in the art to provide multivalent immunogenic compositions or vaccine compositions. By definition, a multivalent immunogenic composition or vaccine composition comprises more than one active immunogenic component originating from, or derived from, the same or at least two different pathogens. Viruses from different genera can vary in stability during the freeze-drying step and subsequent storage period, resulting in a loss of viability or infectivity. In the case of viruses such as dengue, the commonly administered active immunogenic components are live attenuated viruses. To efficiently stimulate the immune system, live attenuated viruses must replicate in the immunized subject. Loss of viability or infectivity can occur during the process of freeze-drying multivalent immunogenic compositions or vaccine compositions, during storage of the compositions, or before administration of the compositions after reconstitution. Thus, stabilizers have been added to such freeze-dried compositions. However, to obtain multivalent immunogenic compositions or vaccine compositions that retain their infectivity and/or viability, a stabilizer that is able to preserve viability and infectivity of different live attenuated pathogens would be particularly advantageous.

Vaccine and immunogenic compositions have had a tremendous impact on public health by reducing morbidity and mortality from a variety of virulent pathogens. However, unintended side effects arising from additives in immunogenic compositions and vaccine compositions continue to pose a potential risk that may outweigh any protective and therapeutic attributes of immunogenic compositions and vaccine compositions.

The present invention addresses the need in the art by providing, inter alia, optimized formulations with stabilizers for freeze-dried live attenuated immunogenic compositions or vaccine compositions, which may comprise live attenuated recombinant dengue virus. These stabilizers may preserve viability and infectivity of these dengue viruses, notably during the freeze-drying process and during a long period of storage of the freeze-dried products at refrigerated temperatures and at room temperature for sufficient period of time to allow the short term excursion from cold chain. Importantly, the presently claimed stabilizers for freeze-dried stabilized live attenuated immunogenic compositions or vaccine compositions of dengue virus are safe and suitable for injection to subjects after reconstitution.

Accordingly, the present invention provides, in one aspect, a stabilizer for a freeze-dried live attenuated recombinant dengue virus immunogenic composition or vaccine composition, which may comprise protein stabilizer, selected from but not restricted to human serum albumin and/or collagen or hydrolyzed collagen or gelatin or hydrolyzed gelatin. The composition may further comprise sugar stabilizer selected from but not restricted to sucrose, mannitol, sorbitol, trehalose, dextran's. Specifically the present invention provides vaccine composition comprising live attenuated dengue virus wherein, the stability of the composition is enhanced by presence of human serum albumin and/or collagen or gelatin or their hydrolyzed versions.

Further the protein stabilizer may be selected from the group of low molecular weight gelatin, hydrolyzed gelatin, collagen, hydrolyzed collagen, recombinant gelatin, recombinant collagen, hydrolyzed collagen derivatives, protein hydrolysates, succinylated gelatin, fish gelatin, bovine gelatin, pork gelatin, avian gelatin. Further the albumin may be selected from the group of human serum albumin, bovine serum albumin and recombinant albumin. In a most preferred embodiment the vaccine is tetravalent. In further preferred embodiment, the dengue virus strains used in the vaccines according to the present invention carry Δ 30 mutations. In still further preferred embodiments, the dengue strains are selected from dengue virus type 1, dengue virus type 2, dengue virus type 3, dengue virus type 4. In still other preferred embodiments, one or more strains of dengue are chimeric comprising dengue 1 backbone or dengue 2 backbone or dengue 3 backbone or dengue 4 backbone. In certain preferred embodiments, the dengue strains have a phenotype which is temperature sensitivity in Vero cells or the human liver cell line HuH-7.

In a preferred embodiment, the present invention provides a vaccine composition comprising live attenuated recombinant dengue virus wherein, the stability of the composition is enhanced by presence of human serum albumin and/or collagen or gelatin. In more preferred embodiments, human serum albumin and/or collagen or gelatin are present in an amount of 10 to 30 mg/0.5 ml. In other preferred embodiment, human serum albumin is present in an amount of 10 to 30 mg/0.5 ml or 10 to 15 mg/0.5 ml, more specifically 12.5 mg/0.5 ml or 10 mg/0.5 ml. In another preferred embodiment, collagen or gelatin is present in an amount of 1 to 30 mg/0.5 ml, more specifically 15 mg/0.5 ml. In other specifically preferred embodiments collagen or gelatin is present in an amount of 12 to 25 mg/0.5 ml, more specifically 15 mg/0.5 ml or 22 mg/0.5 ml.

In a particularly preferred embodiment the vaccine is tetravalent in terms of live attenuated recombinant dengue virus. In another preferred embodiment, the dengue virus carries Δ 30 mutations and/or Δ 31 mutations. In the most preferred embodiment, the dengue strains are selected from dengue virus type 1, dengue virus type 2, dengue virus type 3, dengue virus type 4. In some vaccines within the scope of the current invention, one or more strains of dengue are chimeric comprising dengue 1 backbone or dengue 2 backbone or dengue 3 backbone or dengue 4 backbone. In further embodiments, the dengue strains have a phenotype which is temperature sensitivity in Vero cells or the human liver cell line HuH-7. In most preferred embodiments, the dengue strains are propagated in VERO cells.

In a most preferred embodiment present invention provides a stable lyophilized tetravalent vaccine composition comprising Dengue virus serotype 1 (rDEN 1Δ30), Dengue virus serotype 2 (rDEN 2/4Δ30), Dengue virus serotype 3 (rDEN 3Δ30/31), Dengue virus serotype 4 (rDEN 4Δ30), wherein, the stability of the composition is enhanced by presence of human serum albumin and/or collagen or gelatin. In specific selections the dengue virus is present at a dose of not less than 3.0 $\log_{10}$ PFU per 0.5 ml.

In other preferred embodiments, the vaccines according to the current invention further comprising bulking agents and/or buffering agents. More specifically the bulking agent is selected from a group comprising of lactose, sucrose, mannitol, trehalose and the like and the buffering agents are selected from a group comprising of Potassium dihydrogen phosphate, Di-potassium hydrogen phosphate, monosodium glutamate and the like. Some vaccines could further comprise supplemental media.

In more preferred embodiments, the present invention provides vaccines wherein the final pH of the composition is about 6.0-8.0.

In another preferred embodiment, the dengue virus is present at a dose of not less than 3.0 $\log_{10}$ PFU per 0.5 ml In another embodiment, the stabilizer may further comprise lactose, sucrose, mannitol, trehalose, dextran, maltodextrin, polyvinylpyrrolidone, hydroxyethyl starch, or combinations thereof.

A stabilized vaccine obtained by reconstituting the lyophilized vaccine is also within the scope of the present invention.

In yet another embodiment, the present invention further provides buffering agents for use in the compositions of the invention, which are selected from a group comprising of Potassium dihydrogen phosphate, Di-potassium hydrogen phosphate, monosodium glutamate and the like.

In preferred embodiments the compositions according to the present invention include supplemental media like Dulbecco's Modified Eagle's Medium and Leibovitz L-15 Medium.

Preferred pH of the final vaccine is in the range of 6.0 to 8.0, most preferably is in the range of 7.0±0.5.

More specifically the instant invention relates to a stable tetravalent immunogenic composition comprising a) a first attenuated virus that is immunogenic against dengue serotype 1, b) a second attenuated virus that is immunogenic against dengue serotype 2, c) a third attenuated virus that is immunogenic against dengue serotype 3, and d) a fourth attenuated virus that is immunogenic against dengue serotype 4, wherein each of a), b), c) and d) comprises a nucleic acid comprising i) a first nucleotide sequence encoding at least one structural protein from a first dengue virus, ii) a second nucleotide sequence encoding nonstructural proteins from the first dengue virus or a second dengue virus, and iii) a 3' untranslated region, wherein the 3' untranslated region contains a deletion of about 30 nucleotides corresponding to the TL2 stem-loop structure, and wherein both the 3' untranslated region and the second nucleotide sequence encoding nonstructural proteins are from either the first dengue virus or the second dengue virus. In certain preferred aspects of the invention, the present invention provides vaccine composition according to any of the preceding claims wherein the dengue strains are propagated in VERO cells.

In a preferred embodiment according to the present invention the stable compositions according to the current invention comprises of live attenuated vaccine candidate viruses selected from Dengue virus type 1 (rDEN1 Δ30-1545 and/or rDEN 1/4Δ30), Dengue virus type 2 (rDEN2Δ30-7169 and/or rDEN2/4Δ30-1495, 7163), Dengue virus type 3 (rDEN3/4Δ30 and/or rDEN3-3'D4Δ30 and/or rDEN3Δ30/31), Dengue virus type 4 (rDEN4Δ30-7132, 7163, 8308 and/or rDEN4Δ30-200, 201 and/or rDEN4Δ30-4995.

In a particularly preferred embodiment the present invention is directed to a stable formulation comprising rDEN1d30-1545 03JB186 TD-1A+V2, rDEN2/4d30-1495, 7163 04JBV351 TD-1A+V2 9/1/04, rDEN3Δ30/31-7164 06JBC577 V6+1A1+V2 5/8/08 Joe and 06JBV591 DEN4Δ30-7132,7163,8308 6/8/06 V3-1A1+V2.

In a preferred embodiment, the present invention provides stable lyophilized tetravalent vaccine composition comprising Dengue virus serotype 1 (rDEN 1Δ30), Dengue virus serotype 2 (rDEN 2/4Δ30), Dengue virus serotype 3 (rDEN 3Δ30/31), Dengue virus serotype 4 (rDEN 44Δ30), wherein, the stability of the composition is enhanced by presence of human serum albumin and/or gelatin and/or collagen.

The vaccine formulation of the present invention comprises virus and stabilizer components in amounts from about 10 to about 30 mg per 0.5 ml of a protein stabilizer selected from but not restricted to human serum albumin, collagen and gelatin; from about 10 to about 100 mg per 0.5 ml of a sugar stabilizer selected from but not restricted to lactose, sucrose, mannitol and trehalose and an amount of a physiologically active buffer to adjust the pH from about 6.5 to about 7.5. It is preferred in the present invention that supplement media be added to the composition. In a preferred embodiment human serum albumin and/or collagen or gelatin are present in an amount of 1 to 30 or 10 to 30 mg/0.5 ml. In most preferred embodiment human serum albumin is present in an amount of 10-15 mg/0.5 ml, more preferably 12.5 mg/0.5 ml. In another preferred embodiment collagen or gelatin is present in an amount of 10-30 mg/0.5 ml, more preferably 15 mg/0.5 ml.

According to a preferred embodiment of the invention the vaccine product is a lyophilized powder for reconstitution and intended for subcutaneous administration. The vaccine is formulated in a stabilizer like human serum albumin and lactose monohydrate to which sucrose is added as bulking agent. The vaccine is diluted in buffer comprising of Potassium dihydrogen phosphate ($KH_2PO_4$), Di-potassium hydrogen phosphate ($K_2HPO_4$) & Monosodium glutamate. Dulbecco's Modified Eagle's Medium and or Leibovitz L-15 Medium may be added as media supplement to the final vaccine. The pH of the final vaccine is in the range of 7.0±0.5.

In yet another preferred embodiment the vaccine is formulated in a stabilizer comprising of gelatin and trehalose to which sucrose and mannitol are added as bulking agent. The vaccine is diluted in buffer comprising of Potassium dihydrogen phosphate ($KH_2PO_4$), Di-potassium hydrogen phosphate ($K_2HPO_4$) & Monosodium glutamate. Dulbecco's Modified Eagle's and or Leibovitz L-15 Medium added as media supplement to the final vaccine. The pH of the final vaccine is in the range of 7.0±0.5.

In preferred embodiments the dengue virus in the vaccine composition is present at a dose of NLT 3.0 $log_{10}$ PFU per 0.5 ml.

The present invention further relates to a method of preventing disease caused by dengue virus in a subject comprising administering an effective amount of the vaccine described above to the subject. The vaccines of the invention can be administered as primary prophylactic agents in adults or children at risk of infection, or can be used as secondary agents for treating infected patients. For example, in the case of DEN virus and chimeric DEN viruses, the vaccines can be used in adults or children at risk of DEN virus infection, or can be used as secondary agents for treating DEN virus-infected patients. Examples of patients who can be treated using the DEN virus-related vaccines and methods of the invention include (i) children in areas in which DEN virus is endemic, (ii) foreign travelers, (iii) military personnel, and (iv) patients in areas of a DEN virus epidemic. Moreover, inhabitants of regions into which the disease has been observed to be expanding (e.g., beyond Sri Lanka, East Africa and Latin America), or regions in which it may be observed to expand in the future can be treated according to the invention The present invention also encompasses vaccine kit comprising a first container containing a stabilized vaccine composition described above and a second container containing an aqueous solution for the reconstitution of the vaccine In a particularly preferred embodiment, the present invention is directed to the below formulation

TABLE 1

| S. No. | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 3.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |

| | Excipients | Range |
|---|---|---|
| 1. | Human serum albumin | 10 to 15 mg |
| 2. | Lactose monohydrate | 25 to 50 mg |
| 3. | Sucrose | 3 to 25 mg |
| 4. | Potassium dihydrogen phosphate ($KH_2PO_4$) | ~260 µg |
| 5. | Di-potassium hydrogen phosphate ($K_2HPO_4$) | ~630 µg |
| 6. | Monosodium glutamate | ~460 µg |
| 7. | Dulbecco's Modified Eagle's Medium | ~500 µg |
| 8. | Sterile Water for injection | Q.s. to 0.5 ml |

*Cell substrate used for propagation: VERO cells
[1]PFU: Plaque forming units

In another preferred embodiment the current invention provides the below formulation:

TABLE 2

| S. No. | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 3.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
| | Excipients | Range |
| 1. | Gelatin | 10 to 30 mg |
| 2. | Mannitol | 5 to 25 mg |
| 3. | Trehalose | 4 to 16 mg |
| 4. | Sucrose | 25 to 60 mg |
| 5. | Potassium dihydrogen phosphate ($KH_2PO_4$) | ~260 μg |
| 6. | Di-potassium hydrogen phosphate ($K_2HPO_4$) | ~630 μg |
| 7. | Monosodium glutamate | ~460 μg |
| 8. | Dulbecco's Modified Eagle's Medium | ~500 μg |
| 9. | Sterile Water for injection | Q.s. to 0.5 ml |

*Cell substrate used for propagation: VERO cells
[1]PFU: Plaque forming units

EXAMPLES

Example 1

Composition: The qualitative and quantitative composition of the Dengue Tetravalent Vaccine, Live Attenuated (Recombinant, Lyophilized) is presented in Table 3 below:

TABLE 3

| SN | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 3.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
| | Excipients | Range |
| 1. | Hydrolyzed Gelatin | 22 mg |
| 2. | Mannitol | 15 mg |
| 3. | Trehalose | 8 mg |
| 4. | Sucrose | 37.5 mg |
| 5. | Potassium dihydrogen phosphate ($KH_2PO_4$) | ~260 μg |
| 6. | Di-potassium hydrogen phosphate ($K_2HPO_4$) | ~630 μg |
| 7. | Monosodium glutamate | ~460 μg |
| 8. | Dulbecco's Modified Eagle's Medium | ~500 μg |
| 9. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents.

For preparing the solution, hydrolyzed Gelatin was transferred to Water for Injection (WFI) in a glass bottle and was allowed to disperse to make a clear solution. To the above solution, remaining excipients {Mannitol, Trehalose, Sucrose, Potassium dihydrogen phosphate ($KH_2PO_4$), Di-potassium hydrogen phosphate ($K_2HPO_4$), Monosodium glutamate and Dulbecco's Modified Eagle's Medium} were added, one after the other. The pH of blend was adjusted to 7.0±0.2 using 1.0 N HCl/1.0 N NaOH solution. The resultant blend was filtered using 0.2μ sterilizing grade filter and was chilled to a temperature range of 5±3° C. Afterwards, calculated quantities of specific dengue virus (serotype 1, 2, 3 & 4) were added to the blend and sterile water for injection was added to make up the volume. If required the pH was adjusted again in the range of 7.0±0.2.

Lyophilization Process of Bulk Vaccine

The final bulk vaccine was filled into USP type I, tubular glass vials and the trays containing half stoppered vaccine vials were placed in lyophilizer. The Lyophilization was performed at following parameters:—

The vials were frozen at a temperature in the range of −40° C. and −60° C. for 8 hrs The primary drying was carried out at a temperature of about −50° C. to about −15° C., vacuum in a range of about 20 mtorr to about 800 mtorr for about 50 hrs.

The secondary drying was carried out at a temperature of about +0° C. to about +30° C., vacuum in a range of about 20 mtorr to about 800 mtorr for about 15 hrs.

After completion of process, the vials were stoppered, sealed, labeled and stored at 2-8° C. in a cold room.

Testing Results: The testing results of above example are as follow:

Stability results of Dengue Tetravalent Vaccine, Live Attenuated (Recombinant, Lyophilized)

TABLE 4

Loss of titre ($\log_{10}$ Pfu/0.5 ml) for different serotypes in Dengue Tetravalent Vaccine

| Serotype Name | After Lyophilization | 37 ± 2° C./7 days | 37 ± 2° C./14 days |
|---|---|---|---|
| rDEN 1Δ30 | 0.00 | 0.40 | 0.80 |
| rDEN 2/4Δ30 | 0.00 | 0.00 | 0.30 |
| rDEN 3Δ30/31 | 0.10 | 0.10 | 0.10 |
| rDEN 4Δ30 | 0.00 | 0.00 | 0.40 |

*Note:
If the results of subsequent time interval are higher than or equal to the initial then the loss of titre is consider as 0

Stability results of Dengue Tetravalent Vaccine, Live Attenuated (Recombinant, Lyophilized)

TABLE 5

Loss of Titre ($\log_{10}$ Pfu/0.5 ml) at different storage conditions for Dengue Tetravalent Vaccine (Lyophilized)

| | 25 ± 2° C. | | | 2-8° C. | | | | |
|---|---|---|---|---|---|---|---|---|
| Serotype Name | 15 days | 1 Month | 2 Months | 1 Month | 3 Months | 6 Months | 9 Months | 12 Months |
| rDEN 1Δ30 | 0.40 | 0.80 | 0.60 | 0.30 | 0.50 | 0.40 | 0.60 | 0.40 |
| rDEN 2/4Δ30 | 0.00 | 0.20 | 0.00 | 0.00 | 0.00 | 0.10 | 0.20 | 0.00 |

TABLE 5-continued

Loss of Titre ($Log_{10}$ Pfu/0.5 ml) at different storage conditions for Dengue Tetravalent Vaccine (Lyophilized)

| Serotype Name | 25 ± 2° C. | | | 2-8° C. | | | | |
|---|---|---|---|---|---|---|---|---|
| | 15 days | 1 Month | 2 Months | 1 Month | 3 Months | 6 Months | 9 Months | 12 Months |
| rDEN 3Δ30/31 | 0.10 | 0.10 | 0.60 | 0.10 | 0.10 | 0.10 | 0.20 | 0.20 |
| rDEN 4Δ30 | 0.00 | 0.20 | 0.20 | 0.00 | 0.10 | 0.20 | 0.10 | 0.10 |

*Note: If the results of subsequent time interval are higher than or equal to the initial then the loss of titre is consider as 0

Stability Results of Final Bulk (Liquid)

TABLE 6

| Serotype Name | Loss of Titre ($Log_{10}$ Pfu/0.5 ml) at storage of 2-8° C. for Dengue Vaccine Final bulk solution | | | |
|---|---|---|---|---|
| | 1 day | 2 days | 3 days | 4 days |
| rDEN 1Δ30 | 0.20 | 0.10 | 0.10 | 0.40 |
| rDEN 2/4Δ30 | 0.20 | 0.30 | 0.20 | 0.30 |
| rDEN 3Δ30/31 | 0.10 | 0.20 | 0.70 | 0.70 |
| rDEN 4Δ30 | 0.20 | 0.20 | 0.20 | 0.40 |

Example 2

Composition: The qualitative and quantitative composition of the Dengue Tetravalent Vaccine, Live Attenuated (Recombinant, Lyophilized) is presented in Table 7 below:

TABLE 7

| SN | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 4.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |
| Excipients | | Range |
| 1. | Gelatin | 22 mg |
| 2. | Mannitol | 10 mg |
| 3. | Trehalose | 5 mg |
| 4. | Sucrose | 55 mg |
| 5. | Potassium dihydrogen phosphate ($KH_2PO_4$) | ~260 µg |
| 6. | Di-potassium hydrogen phosphate ($K_2HPO_4$) | ~630 µg |
| 7. | Monosodium glutamate | ~460 µg |
| 8. | Dulbecco's Modified Eagle's Medium | ~750 µg |
| 9. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents.

For preparing the solution, Gelatin was transferred to Water for Injection (WFI) in a glass bottle and was allowed to disperse to make a clear solution. To the above solution, remaining excipients {Mannitol, Trehalose, Sucrose, Potassium dihydrogen phosphate ($KH_2PO_4$), Di-potassium hydrogen phosphate ($K_2HPO_4$), Monosodium glutamate and Dulbecco's Modified Eagle's Medium} were added, one after the other. The pH of blend was adjusted to 7.0±0.2 using 1.0 N HCl/1.0 N NaOH solution. The resultant blend was filtered using 0.2µ sterilizing grade filter and was chilled to a temperature range of 5±3° C. Afterwards, calculated quantities of specific dengue virus (serotype 1, 2, 3 & 4) were added to the blend and sterile water for injection was added to make up the volume. If required the pH was adjusted again in the range of 7.0±0.2.

Lyophilization Process of Bulk Vaccine: As Defined in Example 1.

Example 3

Composition: The qualitative and quantitative composition of the Dengue Tetravalent Vaccine, Live Attenuated (Recombinant, Lyophilized) is presented in Table 8 below:

TABLE 8

| SN | Name of the component | Quantity (Per dose of 0.05 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 4.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |
| Excipients | | Range |
| 1. | Gelatin | 15 mg |
| 2. | Mannitol | 12 mg |
| 3. | Trehalose | 10 mg |
| 4. | Sucrose | 55 mg |
| 5. | Potassium dihydrogen phosphate ($KH_2PO_4$) | ~270 µg |
| 6. | Di-potassium hydrogen phosphate ($K_2HPO_4$) | ~630 µg |
| 7. | Monosodium glutamate | ~480 µg |
| 8. | Leibovitz L-15 Medium | ~850 µg |
| 9. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents.

For preparing the solution, Gelatin was transferred to Water for Injection (WFI) in a glass bottle and was allowed to disperse to make a clear solution. To the above solution, remaining excipients {Mannitol, Trehalose, Sucrose, Potassium dihydrogen phosphate ($KH_2PO_4$), Di-potassium hydrogen phosphate ($K_2HPO_4$), Monosodium glutamate and Leibovitz L-15 Medium} were added, one after the other. The pH of blend was adjusted to 7.0±0.2 using 1.0 N HCl/1.0 N NaOH solution. The resultant blend was filtered using 0.2μ sterilizing grade filter and was chilled to a temperature range of 5±3° C. Afterwards, calculated quantities of specific dengue virus (serotype 1, 2, 3 & 4) were added to the blend and sterile water for injection was added to make up the volume. If required the pH was adjusted again in the range of 7.0±0.2.

Lyophilization Process of Bulk Vaccine: As Defined in Example 1.

Example 4

Composition: The qualitative and quantitative composition of the Dengue Tetravalent Vaccine, Live Attenuated (Recombinant, Lyophilized) is presented in Table 9 below:

TABLE 9

| SN | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 3.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |
| Excipients | | Range |
| 1. | Hydrolyzed Gelatin | 22 mg |
| 2. | Mannitol | 12 mg |
| 3. | Trehalose | 10 mg |
| 4. | Sucrose | 35 mg |
| 5. | Potassium dihydrogen phosphate ($KH_2PO_4$) | ~270 μg |
| 6. | Di-potassium hydrogen phosphate ($K_2HPO_4$) | ~630 μg |
| 7. | Monosodium glutamate | ~480 μg |
| 8. | Leibovitz L-15 Medium | ~850 μg |
| 9. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents.

For preparing the solution, Hydrolyzed Gelatin was transferred to Water for Injection (WFI) in a glass bottle and was allowed to disperse to make a clear solution. To the above solution, remaining excipients {Mannitol, Trehalose, Sucrose, Potassium dihydrogen phosphate ($KH_2PO_4$), Di-potassium hydrogen phosphate ($K_2HPO_4$), Monosodium glutamate and Leibovitz L-15 Medium} were added, one after the other. The pH of blend was adjusted to 7.0±0.2 using 1.0 N HCl/1.0 N NaOH solution. The resultant blend was filtered using 0.2μ sterilizing grade filter and was chilled to a temperature range of 5±3° C. Afterwards, calculated quantities of specific dengue virus (serotype 1, 2, 3 & 4) were added to the blend and sterile water for injection was added to make up the volume. If required the pH was adjusted again in the range of 7.0±0.2.

Lyophilization Process of Bulk Vaccine: As Defined in Example 1.

Example 5

Composition: The qualitative and quantitative composition of the Dengue Tetravalent Vaccine, Live Attenuated (Recombinant, Lyophilized) is presented in Table 10 below:

TABLE 10

| SN | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 3.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |
| Excepients | | Range |
| 1. | Gelatin | 15 mg |
| 2. | Mannitol | 12 mg |
| 3. | Trehalose | 10 mg |
| 4. | Sucrose | 55 mg |
| 5. | Potassium dihydrogen phosphate ($KH_2PO_4$) | ~270 μg |
| 6. | Di-potassium hydrogen phosphate ($K_2HPO_4$) | ~630 μg |
| 7. | Monosodium glutamate | ~480 μg |
| 8. | Leibovitz L-15 Medium | ~850 μg |
| 9. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents.

For preparing the solution, Gelatin was transferred to Water for Injection (WFI) in a glass bottle and was allowed to disperse to make a clear solution. To the above solution, remaining excipients (Mannitol, Trehalose, Sucrose, Potassium dihydrogen phosphate ($KH_2PO_4$), Di-potassium hydrogen phosphate ($K_2HPO_4$), Monosodium glutamate and Leibovitz L-15 Medium} were added, one after the other. The pH of blend was adjusted to 7.0±0.2 using 1.0 N HCl/1.0 N NaOH solution. The resultant blend was filtered using 0.2μ sterilizing grade filter and was chilled to a temperature range of 5±3° C. Afterwards, calculated quantities of specific dengue virus (serotype 1, 2, 3 & 4) were added to the blend and sterile water for injection was added to make up the volume. If required the pH was adjusted again in the range of 7.0±0.2.

Lyophilization Process of Bulk Vaccine: As Defined in Example 1.

Example 6

Composition: The qualitative and quantitative composition of the Dengue Tetravalent Vaccine, Live Attenuated (Recombinant, Lyophilized) is presented in Table 11 below:

TABLE 11

| SN | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 4.0 $log_{10}$ PFU[1] |

TABLE 11-continued

| | | |
|---|---|---|
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |

| Excipients | Range |
|---|---|
| 1. Hydrolyzed Gelatin | 22 mg |
| 2. Mannitol | 20 mg |
| 3. Trehalose | 10 mg |
| 4. Sucrose | 37.5 mg |
| 5. Potassium dihydrogen phosphate ($KH_2PO_4$) | ~270 µg |
| 6. Di-potassium hydrogen phosphate ($K_2HPO_4$) | ~630 µg |
| 7. Monosodium glutamate | ~480 µg |
| 8. Leibovitz L-15 Medium | ~850 µg |
| 9. Dulbecco's Modified Eagle's Medium | ~500 µg |
| 10. Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents.

For preparing the solution, Hydrolyzed Gelatin was transferred to Water for Injection (WFI) in a glass bottle and was allowed to disperse to make a clear solution. To the above solution, remaining excipients {Mannitol, Trehalose, Sucrose, Potassium dihydrogen phosphate ($KH_2PO_4$), Di-potassium hydrogen phosphate ($K_2HPO_4$), Monosodium glutamate, Dulbecco's Modified Eagle's Medium and Leibovitz L-15 Medium} were added, one after the other. The pH of blend was adjusted to 7.0±0.2 using 1.0 N HCl/1.0 N NaOH solution. The resultant blend was filtered using 0.2μ sterilizing grade filter and was chilled to a temperature range of 5±3° C. Afterwards, calculated quantities of specific dengue virus (serotype 1, 2, 3 & 4) were added to the blend and sterile water for injection was added to make up the volume. If required the pH was adjusted again in the range of 7.0±0.2.

Lyophilization Process of Bulk Vaccine: As Defined in Example 1.

Example 7

Composition: The qualitative and quantitative composition of the Dengue Tetravalent Vaccine, Live Attenuated (Recombinant, Lyophilized) is presented in Table 12 below:

TABLE 12

| SN | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 3.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
| Excipients | | Range |
| 1. | Human serum albumin | 12.5 mg |
| 2. | Lactose monohydrate | 37.5 mg |
| 3. | Sucrose | 5 mg |
| 4. | Potassium dihydrogen phosphate ($KH_2PO_4$) | ~260 μg |
| 5. | Di-potassium hydrogen phosphate ($K_2HPO_4$) | ~630 μg |
| 6. | Monosodium glutamate | ~460 μg |
| 7. | Dulbecco's Modified Eagle's Medium | ~500 μg |
| 8. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents.

For preparing the solution, lactose monohydrate was transferred to Water for Injection (WFI) in a glass bottle and was allowed to disperse to make a clear solution. To the above solution, remaining excipients {Sucrose, Potassium dihydrogen phosphate ($KH_2PO_4$), Di-potassium hydrogen phosphate ($K_2HPO_4$), Monosodium glutamate and Dulbecco's Modified Eagle's Medium} were added, one after the other. The pH of blend was adjusted to 7.0±0.2 using 1.0 N HCl/1.0 N NaOH solution. The resultant blend was filtered using 0.2μ sterilizing grade filter and was chilled to a temperature range of 513° C. Afterwards; calculated quantities of sterile human serum albumin solution were added to the blend followed by addition of specific dengue virus (serotype 1, 2, 3 & 4). The Sterile Water For Injection (SWFI) was added to make up the volume. If required the pH was adjusted again in the range of 7.0±0.2.

Lyophilization Process of Bulk Vaccine

The final bulk vaccine was filled into USP type I, tubular glass vials and the trays containing half stoppered vaccine vials were placed in lyophilizer. The Lyophilization was performed at following parameters:—

The vials were frozen at a temperature in the range of −40° C. and −60° C. for 8 hrs The primary drying was carried out at a temperature of about −50° C. to about −15° C., vacuum in a range of about 20 mtorr to about 800 mtorr for about 50 hrs.

The secondary drying was carried out at a temperature of about +0° C. to about +30° C., vacuum in a range of about 20 mtorr to about 800 mtorr for about 15 hrs.

After completion of process, the vials were stoppered, sealed, labeled and stored at 2-8° C. in a cold room.

Testing Results: The testing results of above example are as follow:

Stability Results of Dengue Tetravalent Vaccine, Live Attenuated (Recombinant, Lyophilized)

TABLE 13

| Serotype Name | Loss of titre (Log10 Pfu/0.5 ml) for different serotypes in Dengue Tetravalent Vaccine: After Lyophilization | 37 ± 2° C./7 days | 37 ± 2° C./14 days |
|---|---|---|---|
| rDEN 1Δ30 | 0.10 | 0.40 | 0.90 |
| rDEN 2/4Δ30 | 0.00 | 0.40 | 0.80 |
| rDEN 3Δ30/31 | 0.30 | 0.70 | 1.00 |
| rDEN 4Δ30 | 0.00 | 0.40 | 0.90 |

*Note:
If the results of subsequent time interval are higher than or equal to the initial then the loss of titre is consider as 0

Stability Results of Dengue Tetravalent Vaccine, Live Attenuated (Recombinant, Lyophilized).

TABLE 14

Loss of Titre ($Log_{10}$ Pfu/0.5 ml) at different storage conditions for Dengue Tetravalent Vaccine (Lyophilized)

| Serotype Name | 25 ± 2° C. | | | 2-8° C. | | | | |
| --- | --- | --- | --- | --- | --- | --- | --- | --- |
| | 15 days | 1 Month | 2 Months | 1 Month | 3 Months | 6 Months | 9 Months | 12 Months |
| rDEN 1Δ30 | 0.10 | 0.50 | 0.80 | 0.10 | 0.30 | 0.20 | 0.70 | 0.50 |
| rDEN 2/4Δ30 | 0.20 | 0.30 | 0.50 | 0.10 | 0.20 | 0.30 | 1.00 | 0.80 |
| rDEN 3Δ30/31 | 0.50 | 0.50 | 0.70 | 0.10 | 0.10 | 0.20 | 0.80 | 0.70 |
| rDEN 4Δ30 | 0.30 | 0.50 | 0.70 | 0.20 | 0.30 | 0.50 | 0.90 | 0.60 |

Stability Results of Final Bulk (Liquid)

TABLE 15

| Serotype Name | Loss of Titre ($Log_{10}$ Pfu/0.5 ml) at storage of 2-8° C. for Dengue Vaccine Final bulk solution | | | |
| --- | --- | --- | --- | --- |
| | 1 day | 2 days | 3 days | 4 days |
| rDEN 1Δ30 | 0.00 | 0.00 | 0.10 | 0.50 |
| rDEN 2/4Δ30 | 0.00 | 0.10 | 0.20 | 0.60 |
| rDEN 3Δ30/31 | 0.20 | 0.00 | 0.20 | 0.20 |
| rDEN 4Δ30 | 0.00 | 0.00 | 0.10 | 0.20 |

*Note:
If the results of subsequent time interval are higher than or equal to the initial then the loss of titre is consider as 0.

Example 8

Composition: The qualitative and quantitative composition of the Dengue Tetravalent Vaccine, Live Attenuated (Recombinant, Lyophilized) is presented in Table 16 below:

TABLE 16

| SN | Name of the component | Quantity (Per dose of 0.5 ml) |
| --- | --- | --- |
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 4.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |
| Excipients | | Range |
| 1. | Human serum albumin | 10 mg |
| 2. | Lactose monohydrate | 50 mg |
| 3. | Sucrose | 10 mg |
| 4. | Potassium dihydrogen phosphate ($KH_2PO_4$) | ~260 μg |
| 5. | Di-potassium hydrogen phosphate ($K_2HPO_4$) | ~630 μg |
| 6. | Monosodium glutamate | ~460 μg |
| 7. | Dulbecco's Modified Eagle's Medium | ~600 μg |
| 8. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents. For preparing the solution, lactose monohydrate was transferred to Water for Injection (WFI) in a glass bottle and was allowed to disperse to make a clear solution. To the above solution, remaining excipients {Sucrose, Potassium dihydrogen phosphate ($KH_2PO_4$), Di-potassium hydrogen phosphate ($K_2HPO_4$), Monosodium glutamate and Dulbecco's Modified Eagle's Medium} were added, one after the other. The pH of blend was adjusted to 7.0±0.2 using 1.0 N HCl/1.0 N NaOH solution. The resultant blend was filtered using 0.2μ sterilizing grade filter and was chilled to a temperature range of 5±3° C. Afterwards; calculated quantities of sterile human serum albumin solution were added to the blend followed by addition of specific dengue virus (serotype 1, 2, 3 & 4). The Sterile Water for Injection (SWFI) was added to make up the volume. If required the pH was adjusted again in the range of 7.0±0.2.

Lyophilization Process of Bulk Vaccine: As Defined in Example 1.

Example 9

Composition: The qualitative and quantitative composition of the Dengue Tetravalent Vaccine, Live Attenuated (Recombinant, Lyophilized) is presented in Table 17 below:

TABLE 17

| SN | Name of the component | Quantity (Per dose of 0.5 ml) |
| --- | --- | --- |
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 4.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |
| Excipients | | Range |
| 1. | Human serum albumin | 10 mg |
| 2. | Lactose monohydrate | 25 mg |
| 3. | Sucrose | 6.5 mg |
| 4. | Potassium dihydrogen phosphate ($KH_2PO_4$) | ~260 μg |
| 5. | Di-potassium hydrogen phosphate ($K_2HPO_4$) | ~630 μg |
| 6. | Monosodium glutamate | ~480 μg |
| 7. | Leibovitz L-15 Medium | ~900 μg |
| 8. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents. For preparing the solution, lactose monohydrate was transferred to Water for Injection (WFI) in a glass bottle and was allowed to disperse to make a clear solution. To the above solution, remaining excipients {Sucrose, Potassium dihydrogen phosphate ($KH_2PO_4$), Di-potassium hydrogen phosphate ($K_2HPO_4$), Monosodium glutamate and Leibovitz L-15 Medium} were added, one after the other. The pH of blend was adjusted to 7.0±0.2 using 1.0 N HCl/1.0 N NaOH solution. The resultant blend was filtered using 0.2µ sterilizing grade filter and was chilled to a temperature range of 5±3° C. Afterwards; calculated quantities of sterile human serum albumin solution were added to the blend followed by addition of specific dengue virus (serotype 1, 2, 3 & 4). The Sterile Water For Injection (SWFI) was added to make up the volume. If required the pH was adjusted again in the range of 7.0±0.2.

Lyophilization Process of Bulk Vaccine: As Defined in Example 1.

Example 10

Composition: The qualitative and quantitative composition of the Dengue Tetravalent Vaccine, Live Attenuated (Recombinant, Lyophilized) is presented in Table 18 below:

TABLE 18

| SN | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 3.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |
| Excepients | | Range |
| 1. | Human serum albumin | 14 mg |
| 2. | Lactose | 40 mg |
| 3. | Sucrose | 25 mg |
| 4. | Potassium dihydrogen phosphate ($KH_2PO_4$) | ~280 μg |
| 5. | Di-potassium hydrogen phosphate ($K_2HPO_4$) | ~640 μg |
| 6. | Monosodium glutamate | ~440 μg |
| 7. | Leibovitz L-15 Medium | ~500 μg |
| 8. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents. For preparing the solution, lactose monohydrate was transferred to Water for Injection (WFI) in a glass bottle and was allowed to disperse to make a clear solution. To the above solution, remaining excipients {Sucrose, Potassium dihydrogen phosphate ($KH_2PO_4$), Di-potassium hydrogen phosphate ($K_2HPO_4$), Monosodium glutamate and Leibovitz L-15 Medium) were added, one after the other. The pH of blend was adjusted to 7.0±0.2 using 1.0 N HCl/1.0 N NaOH solution. The resultant blend was filtered using 0.2μ sterilizing grade filter and was chilled to a temperature range of 5±3° C. Afterwards; calculated quantities of sterile human serum albumin solution were added to the blend followed by addition of specific dengue virus (serotype 1, 2, 3 & 4). The Sterile Water For Injection (SWFI) was added to make up the volume. If required the pH was adjusted again in the range of 7.0±0.2.

Lyophilization Process of Bulk Vaccine: As Defined in Example 1.

All patents, publications and abstracts cited above are incorporated herein by reference in their entirety.

Although only a few embodiments of the present invention have been described herein, it should be understood that the present invention can be embodied in many other specific forms without departing from the spirit or scope of the invention as claimed herein. Accordingly, the present examples and embodiments are to be considered as illustrative and not restrictive, and the invention is not to be limited to the details given herein.

Example 11

Composition: The qualitative and quantitative composition of the Dengue Tetravalent Vaccine, Live Attenuated (Recombinant, Lyophilized) is presented in Table 19 below:

TABLE 19

| SN | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 3.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |
| Excepients | | Range |
| 1. | Hydrolyzed Collagen | 22 mg |
| 2. | Mannitol | 15 mg |
| 3. | Trehalose | 8 mg |
| 4. | Sucrose | 37.5 mg |
| 5. | Potassium dihydrogen phosphate ($KH_2PO_4$) | ~260 μg |
| 6. | Di-potassium hydrogen phosphate ($K_2HPO_4$) | ~630 μg |
| 7. | Monosodium glutamate | ~460 μg |
| 8. | Dulbecco's Modified Eagle's Medium | ~500 μg |
| 9. | Sterile Water for Injection | Q.s. to 0.5 ml |

Formulation of Bulk Vaccine

The tetravalent formulation was prepared by mixing live attenuated, recombinant Dengue virus of serotype 1, 2, 3 & 4 with solution containing stabilizer, buffers and bulking agents as elaborated in the table above. For preparation of solution, hydrolyzed collagen was transferred to water for injection (WFI) in a glass bottle and was allowed to disperse to make a clear solution. To the above solution, remaining excipients {Mannitol, Trehalose, Sucrose, Potassium dihydrogen phosphate ($KH_2PO_4$), Di-potassium hydrogen phosphate ($K_2HPO_4$), Monosodium glutamate and Dulbecco's Modified Eagle's Medium} were added, one after the other. The pH of blend was adjusted to 7.0±0.2 using 1.0 N HCl/1.0 N NaOH solution. The resultant blend was filtered using 0.2μ sterilizing grade filter and was chilled to a temperature range of 5±3° C. Afterwards, calculated quantities of specific dengue virus (serotype 1, 2, 3 & 4) were added to the blend and sterile water for injection was added to make up the volume. If required the pH was adjusted again in the range of 7.0±0.2.

Lyophilization Process of Bulk Vaccine

The final bulk vaccine was filled into USP type I, tubular glass vials and the trays containing half stoppered vaccine vials were placed in lyophilizer. The lyophilization was performed at following parameters:—

The vials were frozen at a temperature in the range of −40° C. and −60° C. for 8 hrs The primary drying was carried out at a temperature of about −50° C. to about −15° C., vacuum in a range of about 20 mtorr to about 800 mtorr for about 50 hrs.

The secondary drying was carried out at a temperature of about +0° C. to about +30° C., vacuum in a range of about 20 mtorr to about 800 mtorr for about 15 hrs.

After completion of process, the vials were stoppered, sealed, labeled and stored at 2-8° C. in a cold room.

Testing Results: The testing results of above example are as follow:

Stability results of Dengue Tetravalent Vaccine, Live Attenuated (Recombinant, Lyophilized)

TABLE 20

| Serotype Name | Loss of titre ($Log_{10}$ Pfu/0.5 ml) for different serotypes in Dengue Tetravalent Vaccine | |
|---|---|---|
| | 37 ± 2° C./7 days | 37 ± 2° C./14 days |
| rDEN 1Δ30 | 0.47 | 0.42 |
| rDEN 2/4Δ30 | 0.38 | 0.34 |
| rDEN 3Δ30/31 | 0.17 | 0.17 |
| rDEN 4Δ30 | 0.12 | 0.34 |

*Note:
If the results of subsequent time interval are higher than or equal to the initial then the loss of titre is considered as 0

Stability Results of Dengue Tetravalent Vaccine, Live Attenuated (Recombinant, Lyophilized)

TABLE 21

| | Loss of Titre ($Log_{10}$ Pfu/0.5 ml) at different storage conditions for Dengue Tetravalent Vaccine (Lyophilized) | | | | | |
|---|---|---|---|---|---|---|
| | 25 ± 2° C. | | 2-8° C. | | | |
| Serotype Name | 15 days | 1 Month | 2 Months | 1 Month | 3 Months | 6 Months | 12 Months |
| rDEN 1Δ30 | 0.00 | 0.17 | 0.98 | 0.12 | 0.07 | 0.07 | 0.12 |
| rDEN 2/4Δ30 | 0.17 | 0.72 | 0.70 | 0.38 | 0.10 | 0.31 | 0.29 |
| rDEN 3Δ30/31 | 0.03 | 0.13 | 0.78 | 0.00 | 0.00 | 0.06 | 0.20 |
| rDEN 4Δ30 | 0.15 | 0.69 | 0.39 | 0.09 | 0.09 | 0.00 | 0.09 |

*Note: If the results of subsequent time interval are higher than or equal to the initial then the loss of titre is consider as 0

Example 12

Composition: The qualitative and quantitative composition of the Dengue Tetravalent Vaccine, Live Attenuated (Recombinant, Lyophilized) is presented in Table 22 below

TABLE 22

| SN | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 4.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |

TABLE 22-continued

| Excipients | | Range |
|---|---|---|
| 1. | Collagen | 22 mg |
| 2. | Mannitol | 10 mg |
| 3. | Trehalose | 5 mg |
| 4. | Sucrose | 55 mg |
| 5. | Potassium dihydrogen phosphate ($KH_2PO_4$) | ~260 µg |
| 6. | Di-potassium hydrogen phosphate ($K_2HPO_4$) | ~630 µg |
| 7. | Monosodium glutamate | ~460 µg |
| 8. | Dulbecco's Modified Eagle's Medium | ~750 µg |
| 9. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents.

For preparing the solution, Collagen was transferred to Water for Injection (WFI) in a glass bottle and was allowed to disperse to make a clear solution. To the above solution, remaining excipients {Mannitol, Trehalose, Sucrose, Potassium dihydrogen phosphate ($KH_2PO_4$), Di-potassium hydrogen phosphate ($K_2HPO_4$), Monosodium glutamate and Dulbecco's Modified Eagle's Medium} were added, one after the other. The pH of blend was adjusted to 7.0±0.2 using 1.0 N HCl/1.0 N NaOH solution. The resultant blend was filtered using 0.2µ sterilizing grade filter and was chilled to a temperature range of 5±3° C. Afterwards, calculated quantities of specific dengue virus (serotype 1, 2, 3 & 4) were added to the blend and sterile water for injection was added to make up the volume. If required the pH was adjusted again in the range of 7.0±0.2.

Lyophilization Process of Bulk Vaccine: As Defined in Previous Example.

Example 13

Composition: The qualitative and quantitative composition of the Dengue Tetravalent Vaccine, Live Attenuated (Recombinant, Lyophilized) is presented in Table 23 below.

TABLE 23

| SN | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 4.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |

| Excipients | | Range |
|---|---|---|
| 1. | Hydrolyzed Collagen | 15 mg |
| 2. | Mannitol | 12 mg |
| 3. | Trehalose | 10 mg |
| 4. | Sucrose | 55 mg |
| 5. | Potassium dihydrogen phosphate ($KH_2PO_4$) | ~270 µg |

TABLE 23-continued

| | | |
|---|---|---|
| 6. | Di-potassium hydrogen phosphate (K$_2$HPO$_4$) | ~630 μg |
| 7. | Monosodium glutamate | ~480 μg |
| 8. | Leibovitz L-15 Medium | ~850 μg |
| 9. | Sterile Water for Injection | Q.s. to 0.5 ml |

*Cell substrate used for propagation: VERO cells
[1]PFU: Plaque forming units

Formulation of Bulk Vaccine

The tetravalent formulation was prepared by mixing live attenuated, recombinant Dengue virus of serotype 1, 2, 3 & 4 with solution containing stabilizer, buffers and bulking agents. For preparing the solution, hydrolyzed collagen was transferred to Water for Injection (WFI) in a glass bottle and was allowed to disperse to make a clear solution. To the above solution, remaining excipients {Mannitol, Trehalose, Sucrose, Potassium dihydrogen phosphate ($KH_2PO_4$), Di-potassium hydrogen phosphate ($K_2HPO_4$), Monosodium glutamate and Leibovitz L-15 Medium} were added, one after the other. The pH of blend was adjusted to 7.0±0.2 using 1.0 N HCl/1.0 N NaOH solution. The resultant blend was filtered using 0.2µ sterilizing grade filter and was chilled to a temperature range of 5±3° C. Afterwards, calculated quantities of specific dengue virus (serotype 1, 2, 3 & 4) were added to the blend and sterile water for injection was added to make up the volume. If required the pH was adjusted again in the range of 7.0±0.2.

Lyophilization Process of Bulk Vaccine: As Defined in Previous Example.

We claim:

1. A vaccine composition comprising (a) Tetravalent live attenuated recombinant dengue virus candidate comprising (rDEN 1Δ30), (rDEN 2/4Δ30), (rDEN 3Δ30/31) and (rDEN 4Δ30); and (b) Human serum albumin and/or gelatin or hydrolyzed gelatin and/or collagen or hydrolyzed collagen.

2. The vaccine composition according to claim 1 wherein the dengue strains have a phenotype which is temperature sensitive in Vero cells or the human liver cell line HuH-7.

3. The vaccine composition according to claim 1 further comprises bulking agents and/or buffering agents.

4. The vaccine composition according to claim 3, wherein the bulking agent is selected from a group comprising of lactose, sucrose, mannitol, or trehalose.

5. The vaccine composition according to claim 3, wherein the buffering agents are selected from the group comprising of potassium dihydrogen-phosphate, Dipotassium hydrogen phosphate, or monosodium glutamate.

6. The vaccine composition according to claim 1, further comprises supplemental media.

7. The vaccine composition according to claim 1 wherein the final pH of the composition is about 6-7.

8. The vaccine composition according to claim 1, wherein the said composition is lyophilized.

9. The vaccine composition according to claim 1 wherein the dengue strains are propagated in VERO cells.

10. The vaccine composition according to claim 3, wherein each of the dengue viruses are present at a dose of not less than 3.0 log 10 PFU per 0.5 ml.

11. The vaccine composition according to claim 8, wherein the lyophilized vaccine is reconstituted to obtain a stabilized vaccine.

12. The vaccine composition according to claim 1, wherein human serum albumin and/or gelatin or hydrolyzed gelatin are present in an amount of 1-30 mgs/0.5 ml and/or collagen or hydrolyzed collagen are present in an amount of 1-30 mgs/0.5 ml.

13. The vaccine composition according to claim 12, wherein human serum albumin is present in an amount of 10-15 mg/0.5 ml.

14. The vaccine composition according to claim 13, wherein human serum albumin is present in an amount of 12.5 mg/0.5 ml or 10 mg/0.5 ml.

15. The vaccine composition according to claim 12, gelatin or hydrolyzed gelatin is present in an amount of 12-25 mg/0.5 ml.

16. The vaccine composition according to claim 15, gelatin or hydrolyzed gelatin is present in an amount of 22 mg/0.5 ml or 15 mg/0.5 ml.

17. The vaccine composition according to claim 12, wherein collagen or hydrolyzed collagen is present in an amount of 12-25 mg/0.5 ml.

18. The vaccine composition according to claim 17, wherein collagen or hydrolyzed collagen is present in an amount of 22 mg/0.5 ml or 15 mg/0.5 ml.

19. The vaccine composition according to claim 1, wherein the said composition is a stable lyophilized tetravalent vaccine comprising Dengue virus serotype 1 (rDEN 1Δ30), Dengue virus serotype 2 (rDEN2/4Δ30), Dengue virus serotype 3 (rDEN 3Δ30/31) and Dengue virus serotype 4 (rDEN 4Δ30), and human serum albumin and/or gelatin or hydrolyzed gelatin and/or collagen or hydrolyzed collagen.

20. The vaccine composition according to claim 19, wherein each of the dengue viruses are present at a dose of not less than 3.0 log 10PFU per 0.5 ml.

21. The vaccine composition according to claim 19, wherein the composition is selected from the group consisting of the compositions in the following Tables:

TABLE 1

| S. No. | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 3.0 $log_{10}$ PFU[1] |
| 3. | Dengue virus serotype 3 (rDEN 3Δ30/31)* | NLT 3.0 $log_{10}$ PFU[1] |
| 4. | Dengue virus serotype 4 (rDEN 4Δ30)* | NLT 3.0 $log_{10}$ PFU[1] |
| | Excipients | Range |
| 1. | Human serum albumin | 10 to 15 mg |
| 2. | Lactose monohydrate | 25 to 50 mg |
| 3. | Sucrose | 3 to 25 mg |
| 4. | Potassium dihydrogen phosphate ($KH_2PO_4$) | ~260 µg |
| 5. | Di-potassium hydrogen phosphate ($K_2HPO_4$) | ~630 µg |
| 6. | Monosodium glutamate | ~460 µg |
| 7. | Dulbecco's Modified Eagle's Medium | ~500 µg |
| 8. | Water for injection | Q.s. to 0.5 ml |

TABLE 2

| S. No. | Name of the component | Quantity (Per dose of 0.5 ml) |
|---|---|---|
| 1. | Dengue virus serotype 1 (rDEN 1Δ30)* | NLT 3.0 $log_{10}$ PFU[1] |
| 2. | Dengue virus serotype 2 (rDEN 2/4Δ30)* | NLT 3.0 $log_{10}$ PFU[1] |

TABLE 2-continued

| S. No. | Name of the component | Quantity (Per dose of 0.5 ml) |
|---|---|---|
| 3. | Dengue virus serotype 3 (rDEN 3Δ30/31)* | NLT 3.0 log$_{10}$ PFU[1] |
| 4. | Dengue virus serotype 4 (rDEN 4Δ30)* | NLT 3.0 log$_{10}$ PFU[1] |

| | Excipients | Range |
|---|---|---|
| 1. | Gelatin | 10 to 30 mg |
| 2. | Mannitol | 5 to 25 mg |
| 3. | Trehalose | 4 to 16 mg |
| 4. | Sucrose | 25 to 60 mg |
| 5. | Potassium dihydrogen phosphate (KH$_2$PO$_4$) | ~260 µg |
| 6. | Di-potassium hydrogen phosphate (K$_2$HPO$_4$) | ~630 µg |
| 7. | Monosodium glutamate | ~460 µg |
| 8. | Dulbecco's Modified Eagle's Medium | ~500 µg |
| 9. | Water for injection | Q.s. to 0.5 ml |

TABLE 3

| S. No. | Name of the component | Quantity (Per dose of 0.5 ml) |
|---|---|---|
| 1. | Dengue virus serotype 1 (rDEN 1Δ30)* | NLT 3.0 log$_{10}$ PFU[1] |
| 2. | Dengue virus serotype 2 (rDEN 2/4Δ30)* | NLT 3.0 log$_{10}$ PFU[1] |
| 3. | Dengue virus serotype 3 (rDEN 3Δ30/31)* | NLT 3.0 log$_{10}$ PFU[1] |
| 4. | Dengue virus serotype 4 (rDEN 4Δ30)* | NLT 3.0 log$_{10}$ PFU[1] |

| | Excipients | Range |
|---|---|---|
| 1. | Hydrolyzed Gelatin | 22 mg |
| 2. | Mannitol | 15 mg |
| 3. | Trehalose | 8 mg |
| 4. | Sucrose | 37.5 mg |
| 5. | Potassium dihydrogen phosphate (KH$_2$PO$_4$) | ~260 µg |
| 6. | Di-potassium hydrogen phosphate (K$_2$HPO$_4$) | ~630 µg |
| 7. | Monosodium glutamate | ~460 µg |
| 8. | Dulbecco's Modified Eagle's Medium | ~500 µg |
| 9. | Sterile Water for Injection | Q.s. to 0.5 ml |

TABLE 7

| S. No. | Name of the component | Quantity (Per dose of 0.5 ml) |
|---|---|---|
| 1. | Dengue virus serotype 1 (rDEN 1Δ30)* | NLT 3.0 log$_{10}$ PFU[1] |
| 2. | Dengue virus serotype 2 (rDEN 2/4Δ30)* | NLT 4.0 log$_{10}$ PFU[1] |
| 3. | Dengue virus serotype 3 (rDEN 3Δ30/31)* | NLT 3.0 log$_{10}$ PFU[1] |
| 4. | Dengue virus serotype 4 (rDEN 4Δ30)* | NLT 3.0 log$_{10}$ PFU[1] |

| | Excipients | Range |
|---|---|---|
| 1. | Gelatin | 22 mg |
| 2. | Mannitol | 10 mg |
| 3. | Trehalose | 5 mg |
| 4. | Sucrose | 55 mg |
| 5. | Potassium dihydrogen phosphate (KH$_2$PO$_4$) | ~260 µg |
| 6. | Di-potassium hydrogen phosphate (K$_2$HPO$_4$) | ~630 µg |
| 7. | Monosodium glutamate | ~460 µg |
| 8. | Dulbecco's Modified Eagle's Medium | ~750 µg |
| 9. | Sterile Water for Injection | Q.s. to 0.5 ml |

TABLE 8

| S. No. | Name of the component | Quantity (Per dose of 0.5 ml) |
|---|---|---|
| 1. | Dengue virus serotype 1 (rDEN 1Δ30)* | NLT 3.0 log$_{10}$ PFU[1] |
| 2. | Dengue virus serotype 2 (rDEN 2/4Δ30)* | NLT 4.0 log$_{10}$ PFU[1] |

TABLE 8-continued

| S. No. | Name of the component | Quantity (Per dose of 0.5 ml) |
|---|---|---|
| 3. | Dengue virus serotype 3 (rDEN 3Δ30/31)* | NLT 3.0 log$_{10}$ PFU[1] |
| 4. | Dengue virus serotype 4 (rDEN 4Δ30)* | NLT 3.0 log$_{10}$ PFU[1] |

| | Excipients | Range |
|---|---|---|
| 1. | Gelatin | 15 mg |
| 2. | Mannitol | 12 mg |
| 3. | Trehalose | 10 mg |
| 4. | Sucrose | 55 mg |
| 5. | Potassium dihydrogen phosphate (KH$_2$PO$_4$) | ~270 µg |
| 6. | Di-potassium hydrogen phosphate (K$_2$HPO$_4$) | ~630 µg |
| 7. | Monosodium glutamate | ~480 µg |
| 8. | Leibovitz L-15 Medium | ~850 µg |
| 9. | Sterile Water for Injection | Q.s. to 0.5 ml |

TABLE 9

| S. No. | Name of the component | Quantity (Per dose of 0.5 ml) |
|---|---|---|
| 1. | Dengue virus serotype 1 (rDEN 1Δ30)* | NLT 3.0 log$_{10}$ PFU[1] |
| 2. | Dengue virus serotype 2 (rDEN 2/4Δ30)* | NLT 3.0 log$_{10}$ PFU[1] |
| 3. | Dengue virus serotype 3 (rDEN 3Δ30/31)* | NLT 3.0 log$_{10}$ PFU[1] |
| 4. | Dengue virus serotype 4 (rDEN 4Δ30)* | NLT 3.0 log$_{10}$ PFU[1] |

| | Excipients | Range |
|---|---|---|
| 1. | Hydrolyzed Gelatin | 22 mg |
| 2. | Mannitol | 12 mg |
| 3. | Trehalose | 10 mg |
| 4. | Sucrose | 35 mg |
| 5. | Potassium dihydrogen phosphate (KH$_2$PO$_4$) | ~270 µg |
| 6. | Di-potassium hydrogen phosphate (K$_2$HPO$_4$) | ~630 µg |
| 7. | Monosodium glutamate | ~480 µg |
| 8. | Leibovitz L-15 Medium | ~850 µg |
| 9. | Sterile Water for Injection | Q.s. to 0.5 ml |

TABLE 10

| S. No. | Name of the component | Quantity (Per dose of 0.5 ml) |
|---|---|---|
| 1. | Dengue virus serotype 1 (rDEN 1Δ30)* | NLT 3.0 log$_{10}$ PFU[1] |
| 2. | Dengue virus serotype 2 (rDEN 2/4Δ30)* | NLT 3.0 log$_{10}$ PFU[1] |
| 3. | Dengue virus serotype 3 (rDEN 3Δ30/31)* | NLT 3.0 log$_{10}$ PFU[1] |
| 4. | Dengue virus serotype 4 (rDEN 4Δ30)* | NLT 3.0 log$_{10}$ PFU[1] |

| | Excipients | Range |
|---|---|---|
| 1. | Gelatin | 15 mg |
| 2. | Mannitol | 12 mg |
| 3. | Trehalose | 10 mg |
| 4. | Sucrose | 55 mg |
| 5. | Potassium dihydrogen phosphate (KH$_2$PO$_4$) | ~270 µg |
| 6. | Di-potassium hydrogen phosphate (K$_2$HPO$_4$) | ~630 µg |
| 7. | Monosodium glutamate | ~480 µg |
| 8. | Leibovitz L-15 Medium | ~850 µg |
| 9. | Sterile Water for Injection | Q.s. to 0.5 ml |

TABLE 11

| S. No. | Name of the component | Quantity (Per dose of 0.5 ml) |
|---|---|---|
| 1. | Dengue virus serotype 1 (rDEN 1Δ30)* | NLT 3.0 log$_{10}$ PFU[1] |
| 2. | Dengue virus serotype 2 (rDEN 2/4Δ30)* | NLT 4.0 log$_{10}$ PFU[1] |
| 3. | Dengue virus serotype 3 (rDEN 3Δ30/31)* | NLT 3.0 log$_{10}$ PFU[1] |
| 4. | Dengue virus serotype 4 (rDEN 4Δ30)* | NLT 3.0 log$_{10}$ PFU[1] |

TABLE 11-continued

| S. No. | Name of the component | Quantity (Per dose of 0.5 ml) |
|---|---|---|
| | Excipients | Range |
| 1. | Hydrolyzed Gelatin | 22 mg |
| 2. | Mannitol | 20 mg |
| 3. | Trehalose | 10 mg |
| 4. | Sucrose | 37.5 mg |
| 5. | Potassium dihydrogen phosphate ($KH_2PO_4$) | ~270 µg |
| 6. | Di-potassium hydrogen phosphate ($K_2HPO_4$) | ~630 µg |
| 7. | Monosodium glutamate | ~480 µg |
| 8. | Leibovitz L-15 Medium | ~850 µg |
| 9. | Dulbecco's Modified Eagle's Medium | ~500 µg |
| 10. | Sterile Water for Injection | Q.s. to 0.5 ml |

TABLE 12

| S. No. | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 3.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
| | Excipients | Range |
| 1. | Human Serum Albumin | 12.5 mg |
| 2. | Lactose monohydrate | 37.5 mg |
| 3. | Sucrose | 5 mg |
| 4. | Potassium dihydrogen phosphate ($KH_2PO_4$) | ~260 µg |
| 5. | Di-potassium hydrogen phosphate ($K_2HPO_4$) | ~630 µg |
| 6. | Monosodium glutamate | ~460 µg |
| 7. | Dulbecco's Modified Eagle's Medium | ~500 µg |
| 8. | Sterile Water for Injection | Q.s. to 0.5 ml |

TABLE 16

| S. No. | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 4.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
| | Excipients | Range |
| 1. | Human serum albumin | 10 mg |
| 2. | Lactose monohydrate | 50 mg |
| 3. | Sucrose | 10 mg |
| 4. | Potassium dihydrogen phosphate ($KH_2PO_4$) | ~260 µg |
| 5. | Di-potassium hydrogen phosphate ($K_2HPO_4$) | ~630 µg |
| 6. | Monosodium glutamate | ~460 µg |
| 7. | Dulbecco's Modified Eagle's Medium | ~600 µg |
| 8. | Sterile Water for Injection | Q.s. to 0.5 ml |

TABLE 17

| S. No. | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 4.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
| | Excipients | Range |
| 1. | Human serum albumin | 10 mg |
| 2. | Lactose monohydrate | 25 mg |
| 3. | Sucrose | 6.5 mg |

TABLE 17-continued

| S. No. | Name of the component | Quantity (Per dose of 0.5 ml) |
|---|---|---|
| 4. | Potassium dihydrogen phosphate ($KH_2PO_4$) | ~260 µg |
| 5. | Di-potassium hydrogen phosphate ($K_2HPO_4$) | ~630 µg |
| 6. | Monosodium glutamate | ~480 µg |
| 7. | Leibovitz L-15 Medium | ~900 µg |
| 8. | Sterile Water for Injection | Q.s. to 0.5 ml |

TABLE 18

| S. No. | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 3.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
| | Excipients | Range |
| 1. | Human serum albumin | 14 mg |
| 2. | Lactose | 40 mg |
| 3. | Sucrose | 25 mg |
| 4. | Potassium dihydrogen phosphate ($KH_2PO_4$) | ~280 µg |
| 5. | Di-potassium hydrogen phosphate ($K_2HPO_4$) | ~640 µg |
| 6. | Monosodium glutamate | ~440 µg |
| 7. | Leibovitz L-15 Medium | ~500 µg |
| 8. | Sterile Water for Injection | Q.s. to 0.5 ml |

TABLE 19

| S. No. | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 3.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
| | Excipients | Range |
| 1. | Hydrolyzed Collagen | 22 mg |
| 2. | Mannitol | 15 mg |
| 3. | Trehalose | 8 mg |
| 4. | Sucrose | 37.5 mg |
| 5. | Potassium dihydrogen phosphate ($KH_2PO_4$) | ~260 µg |
| 6. | Di-potassium hydrogen phosphate ($K_2HPO_4$) | ~630 µg |
| 7. | Monosodium glutamate | ~460 µg |
| 8. | Dulbecco's Modified Eagle's Medium | ~500 µg |
| 9. | Sterile Water for Injection | Q.s. to 0.5 ml |

TABLE 22

| S. No. | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 4.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
| | Excipients | Range |
| 1. | Collagen | 22 mg |
| 2. | Mannitol | 10 mg |
| 3. | Trehalose | 5 mg |
| 4. | Sucrose | 55 mg |
| 5. | Potassium dihydrogen phosphate ($KH_2PO_4$) | ~260 µg |
| 6. | Di-potassium hydrogen phosphate ($K_2HPO_4$) | ~630 µg |
| 7. | Monosodium glutamate | ~460 µg |

TABLE 22-continued

| S. No. | Name of the component | Quantity (Per dose of 0.5 ml) |
|---|---|---|
| 8. | Dulbecco's Modified Eagle's Medium | ~750 µg |
| 9. | Sterile Water for Injection | Q.s. to 0.5 ml |

TABLE 23

| S. No. | Name of the component | Quantity (Per dose of 0.5 ml) |
|---|---|---|
| 1. | Dengue virus serotype 1 (rDEN 1Δ30)* | NLT 3.0 $\log_{10}$ PFU[1] |
| 2. | Dengue virus serotype 2 (rDEN 2/4Δ30)* | NLT 4.0 $\log_{10}$ PFU[1] |
| 3. | Dengue virus serotype 3 (rDEN 3Δ30/31)* | NLT 3.0 $\log_{10}$ PFU[1] |
| 4. | Dengue virus serotype 4 (rDEN 4Δ30)* | NLT 3.0 $\log_{10}$ PFU[1] |
|  | Excipients | Range |
| 1. | Hydrolyzed Collagen | 15 mg |
| 2. | Mannitol | 12 mg |
| 3. | Trehalose | 10 mg |
| 4. | Sucrose | 55 mg |
| 5. | Potassium dihydrogen phosphate ($KH_2PO_4$) | ~270 µg |
| 6. | Di-potassium hydrogen phosphate ($K_2HPO_4$) | ~630 µg |
| 7. | Monosodium glutamate | ~480 µg |
| 8. | Leibovitz L-15 Medium | ~850 µg |
| 9. | Sterile Water for Injection | Q.s. to 0.5 ml. |

22. A vaccine kit comprising a first container containing a stabilized vaccine composition according to claim 19 and a second container containing an aqueous solution for the reconstitution of the vaccine.

\* \* \* \* \*